United States Patent
Roy et al.

(10) Patent No.: US 11,998,391 B1
(45) Date of Patent: *Jun. 4, 2024

(54) METHOD AND APPARATUS FOR COMPOSITION OF ULTRASOUND IMAGES WITH INTEGRATION OF "THICK-SLICE" 3-DIMENSIONAL ULTRASOUND IMAGING ZONE(S) AND 2-DIMENSIONAL ULTRASOUND ZONE(S) UTILIZING A MULTI-ZONE, MULTI-FREQUENCY ULTRASOUND IMAGE RECONSTRUCTION SCHEME WITH SUB-ZONE BLENDING

(71) Applicant: yoR Labs, Inc., Beaverton, OR (US)

(72) Inventors: Anshumali Roy, Portland, OR (US);
Chung Ping Cheung, Burnaby (CA);
Clark D. Brooks, Hillsboro, OR (US);
Colin Doolittle, Portland, OR (US);
Andrei Kniazev, Happy Valley, OR (US)

(73) Assignee: YOR LABS, INC., Beaverton, OR (US)

( * ) Notice: Subject to any disclaimer, the term of this patent is extended or adjusted under 35 U.S.C. 154(b) by 135 days.

This patent is subject to a terminal disclaimer.

(21) Appl. No.: 17/301,413

(22) Filed: Apr. 1, 2021

Related U.S. Application Data

(60) Provisional application No. 63/004,354, filed on Apr. 2, 2020.

(51) Int. Cl.
*A61B 8/08* (2006.01)
*A61B 8/00* (2006.01)

(52) U.S. Cl.
CPC ............ *A61B 8/483* (2013.01); *A61B 8/4494* (2013.01); *A61B 8/5207* (2013.01)

(58) Field of Classification Search
CPC ...... A61B 8/483; A61B 8/4494; A61B 8/5207
See application file for complete search history.

(56) References Cited

U.S. PATENT DOCUMENTS

| | | | |
|---|---|---|---|
| 4,998,132 A | 3/1991 | Kurogane |
| 5,617,371 A | 4/1997 | Williams |

(Continued)

FOREIGN PATENT DOCUMENTS

| | | |
|---|---|---|
| AU | 2018250516 | 11/2018 |
| EP | 2 288 284 | 5/2016 |

(Continued)

OTHER PUBLICATIONS

Lin, Cheng-Hsien, Yung-Nien Sun, and Chii-Jeng Lin. "A motion compounding technique for speckle reduction in ultrasound images." Journal of digital imaging 23.3 (2010): 246-257. (Year: 2010).*

(Continued)

*Primary Examiner* — Serkan Akar
*Assistant Examiner* — Neshat Baset
(74) *Attorney, Agent, or Firm* — KNOBBE, MARTENS, OLSON & BEAR LLP

(57) ABSTRACT

Systems and methods of 3D ultrasound imaging with one or more "thick-slice" 3D ultrasound imaging zones and one or more 2D ultrasound zones using a multi-zone, multi-frequency image reconstruction scheme with subzone blending. The first zone can be a thick-slice imaging zone and the second and third zones are 2D imaging zones. The first zone and the second zone can be thick-slice imaging zones and the third zone can be a 2D imaging zone. The first zone can be a 2D imaging zone, the second zone can be a thick-slice imaging zone and the third zone can be a 2D imaging zone. A method includes imaging a first zone using plane wave imaging, a second zone using tissue harmonic imaging, and a third zone using fundamental and subharmonic deep (Continued)

imaging. The depth of each zone can vary based on the ultrasonic array and the F# used for imaging the zone.

18 Claims, 14 Drawing Sheets

(56) References Cited

U.S. PATENT DOCUMENTS

| | | | |
|---|---|---|---|
| 5,903,516 A | 5/1999 | Greenleaf et al. | |
| 5,908,389 A * | 6/1999 | Roundhill | A61B 8/463 |
| | | | 600/443 |
| 6,031,529 A | 2/2000 | Migos | |
| 6,063,030 A | 5/2000 | Vara et al. | |
| 6,120,450 A | 9/2000 | Li | |
| 6,123,670 A * | 9/2000 | Mo | G01S 15/8954 |
| | | | 600/447 |
| 6,132,374 A | 10/2000 | Hossack et al. | |
| 6,400,981 B1 | 6/2002 | Govari | |
| 6,607,489 B2 | 8/2003 | Hoctor | |
| 6,690,963 B2 | 2/2004 | Ben Haim et al. | |
| 6,908,434 B1 | 6/2005 | Jenkins et al. | |
| 7,090,639 B2 | 8/2006 | Govari | |
| 7,423,578 B1 | 9/2008 | Tietjen | |
| 7,604,601 B2 | 10/2009 | Altmann et al. | |
| 7,648,462 B2 | 1/2010 | Jenkins et al. | |
| 7,667,639 B2 | 2/2010 | Cheng et al. | |
| 7,682,358 B2 | 3/2010 | Gullickson et al. | |
| 7,750,849 B2 | 7/2010 | Hjelmstad | |
| 7,831,076 B2 | 11/2010 | Altmann et al. | |
| 7,860,553 B2 | 12/2010 | Govari et al. | |
| 7,918,793 B2 | 4/2011 | Altmann et al. | |
| 7,996,060 B2 | 8/2011 | Trofimov et al. | |
| 8,075,486 B2 | 12/2011 | Tal | |
| 8,285,364 B2 | 10/2012 | Barbagli et al. | |
| 8,390,438 B2 | 3/2013 | Olson et al. | |
| 8,449,467 B2 | 5/2013 | Wilser et al. | |
| 8,517,946 B2 | 8/2013 | Kim | |
| 8,676,290 B2 | 3/2014 | Tegg | |
| 8,690,871 B2 | 4/2014 | Partlett et al. | |
| 8,702,612 B2 | 4/2014 | Hendriks et al. | |
| 8,989,842 B2 | 3/2015 | Li et al. | |
| 9,030,354 B2 | 5/2015 | Natarajan | |
| 9,055,883 B2 | 6/2015 | Tgavalekos et al. | |
| 9,095,682 B2 | 8/2015 | Romoscanu | |
| 9,132,913 B1 | 9/2015 | Shapiro et al. | |
| 9,179,890 B2 | 11/2015 | Ionasec et al. | |
| 9,211,160 B2 | 12/2015 | Pivotto et al. | |
| 9,261,595 B2 | 2/2016 | Garbini et al. | |
| 9,323,445 B2 | 4/2016 | Kritt et al. | |
| 9,342,156 B2 | 5/2016 | Huh | |
| 9,922,554 B2 | 3/2018 | Mikuni et al. | |
| 9,931,487 B2 | 4/2018 | Quinn et al. | |
| 9,986,969 B2 | 6/2018 | Call et al. | |
| 10,183,149 B2 | 1/2019 | Tegg et al. | |
| 10,206,652 B2 | 2/2019 | Deno et al. | |
| 10,368,951 B2 | 8/2019 | Moll et al. | |
| 10,401,492 B2 | 9/2019 | Brooks | |
| 10,405,830 B2 | 9/2019 | Garbini et al. | |
| 10,463,439 B2 | 11/2019 | Joseph et al. | |
| 10,499,882 B2 | 12/2019 | Hunter et al. | |
| 10,537,307 B2 | 1/2020 | Yang | |
| 10,555,780 B2 | 2/2020 | Tanner et al. | |
| 10,624,612 B2 | 4/2020 | Sumi | |
| 11,344,281 B2 | 5/2022 | Morisse et al. | |
| 11,547,386 B1 * | 1/2023 | Roy | G01S 15/895 |
| 2002/0173721 A1 | 11/2002 | Grunwald | |
| 2002/0173722 A1 | 11/2002 | Hoctor et al. | |
| 2003/0007598 A1 * | 1/2003 | Wang | A61B 6/463 |
| | | | 378/37 |
| 2003/0055334 A1 | 3/2003 | Steinbacher et al. | |
| 2003/0055337 A1 * | 3/2003 | Lin | G01S 15/8915 |
| | | | 600/459 |
| 2004/0102700 A1 | 5/2004 | Asafusa | |
| 2005/0288588 A1 * | 12/2005 | Weber | A61B 8/483 |
| | | | 600/447 |
| 2007/0027733 A1 | 2/2007 | Balle | |
| 2007/0174772 A1 | 7/2007 | Gorman | |
| 2007/0200760 A1 | 8/2007 | Hjelmstad | |
| 2007/0239001 A1 | 10/2007 | Mehi et al. | |
| 2007/0259158 A1 | 11/2007 | Friedman et al. | |
| 2008/0012753 A1 | 1/2008 | Cheng | |
| 2008/0114239 A1 | 5/2008 | Randall et al. | |
| 2008/0215046 A1 | 9/2008 | Messing et al. | |
| 2008/0306385 A1 | 12/2008 | Jago | |
| 2009/0043206 A1 * | 2/2009 | Towfiq | G01S 15/8993 |
| | | | 600/447 |
| 2009/0118620 A1 | 5/2009 | Tgavalekos et al. | |
| 2009/0271704 A1 | 10/2009 | Cohen | |
| 2010/0030076 A1 * | 2/2010 | Vortman | G01S 7/5209 |
| | | | 601/2 |
| 2010/0081938 A1 * | 4/2010 | Kato | A61B 8/481 |
| | | | 600/458 |
| 2010/0146431 A1 | 6/2010 | Raji et al. | |
| 2010/0160784 A1 | 6/2010 | Poland | |
| 2010/0168580 A1 * | 7/2010 | Thiele | G01S 15/8993 |
| | | | 600/447 |
| 2010/0251823 A1 | 10/2010 | Adachi | |
| 2011/0077524 A1 | 3/2011 | Oshiki et al. | |
| 2011/0137132 A1 | 6/2011 | Gustafson | |
| 2011/0208052 A1 | 8/2011 | Entrekin | |
| 2012/0075208 A1 | 3/2012 | Tamiya et al. | |
| 2012/0157851 A1 | 6/2012 | Zwirn | |
| 2012/0254747 A1 | 10/2012 | Bocirnea | |
| 2013/0227052 A1 | 8/2013 | Wenzel | |
| 2013/0234891 A1 | 9/2013 | Natarajan et al. | |
| 2013/0238990 A1 | 9/2013 | Ubillos et al. | |
| 2013/0253317 A1 | 9/2013 | Gauthier | |
| 2013/0274712 A1 | 10/2013 | Schecter et al. | |
| 2014/0035916 A1 | 2/2014 | Murphy | |
| 2014/0046188 A1 | 2/2014 | Yen et al. | |
| 2014/0058266 A1 | 2/2014 | Call et al. | |
| 2014/0087342 A1 | 3/2014 | Campanatti, Jr. | |
| 2014/0164965 A1 | 6/2014 | Lee et al. | |
| 2014/0189560 A1 | 7/2014 | Caspi | |
| 2014/0219059 A1 | 8/2014 | Younghouse | |
| 2015/0019488 A1 | 1/2015 | Higginson et al. | |
| 2015/0065877 A1 * | 3/2015 | Orderud | A61B 8/466 |
| | | | 600/438 |
| 2015/0082251 A1 | 3/2015 | Lam | |
| 2015/0293223 A1 | 10/2015 | Park et al. | |
| 2016/0016015 A1 * | 1/2016 | Slayton | A61H 23/0245 |
| | | | 601/3 |
| 2016/0054901 A1 | 2/2016 | Yang et al. | |
| 2016/0157824 A1 | 6/2016 | Park et al. | |
| 2016/0161589 A1 | 6/2016 | Benattar | |
| 2016/0161594 A1 | 6/2016 | Benattar | |
| 2016/0161595 A1 | 6/2016 | Benattar | |
| 2016/0165338 A1 | 6/2016 | Benattar | |
| 2016/0165341 A1 | 6/2016 | Benattar | |
| 2016/0338676 A1 | 11/2016 | Berger et al. | |
| 2017/0090571 A1 | 3/2017 | Bjaerum | |
| 2017/0153801 A1 | 6/2017 | Kim et al. | |
| 2017/0307755 A1 | 10/2017 | Brooks | |
| 2017/0343655 A1 * | 11/2017 | Solek | G01S 15/8927 |
| 2017/0343668 A1 | 11/2017 | Brooks et al. | |
| 2018/0000449 A1 | 1/2018 | Moore et al. | |
| 2018/0000453 A1 | 1/2018 | Hunter et al. | |
| 2018/0055483 A1 | 3/2018 | Hunter | |
| 2018/0064415 A1 | 3/2018 | Zhai et al. | |
| 2018/0361145 A1 | 12/2018 | Mahapatra et al. | |
| 2019/0245310 A1 | 8/2019 | Medina et al. | |
| 2019/0261953 A1 | 8/2019 | Honjo et al. | |
| 2019/0307427 A1 | 10/2019 | Levy et al. | |
| 2019/0324139 A1 | 10/2019 | Brooks | |
| 2019/0353975 A1 | 11/2019 | DiDomenico | |
| 2020/0046321 A1 | 2/2020 | Duda | |
| 2020/0060646 A1 | 2/2020 | Lindenroth et al. | |
| 2020/0170662 A1 | 6/2020 | Vardi | |
| 2020/0178928 A1 | 6/2020 | Park et al. | |
| 2020/0183004 A1 * | 6/2020 | Gong | G01S 15/8977 |
| 2020/0205783 A1 | 7/2020 | Shiran | |
| 2020/0268351 A1 | 8/2020 | Chiang | |

(56) References Cited

U.S. PATENT DOCUMENTS

| | | |
|---|---|---|
| 2020/0281565 A1 | 9/2020 | Yee et al. |
| 2020/0315592 A1* | 10/2020 | Soleimani ............ A61B 8/4427 |
| 2021/0007710 A1 | 1/2021 | Douglas |
| 2021/0038334 A1 | 2/2021 | Hsu et al. |
| 2021/0125503 A1 | 4/2021 | Henry et al. |
| 2021/0177379 A1 | 6/2021 | Kolen et al. |
| 2021/0338208 A1* | 11/2021 | Nguyen ............. G01S 15/8925 |
| 2021/0401508 A1 | 12/2021 | Zhao |
| 2022/0061811 A1 | 3/2022 | Terleski |
| 2022/0061814 A1 | 3/2022 | Morrise |
| 2022/0151591 A1 | 5/2022 | Morrise |
| 2022/0156094 A1 | 5/2022 | Morrise |
| 2023/0059122 A1 | 2/2023 | Pellegrino |

FOREIGN PATENT DOCUMENTS

| | | |
|---|---|---|
| EP | 3 275 478 | 1/2018 |
| EP | 2 707 076 | 11/2018 |
| EP | 3 050 214 | 3/2019 |
| EP | 2 632 318 | 11/2019 |
| EP | 3 518 777 | 3/2021 |
| WO | WO 2012/088535 | 6/2012 |
| WO | WO 2020/0049012 | 3/2020 |
| WO | WO 2020/252416 | 12/2020 |

OTHER PUBLICATIONS

Bradley, Aug. 2008, Retrospective transmit beamformation: Acuson SC2000 volume imaging ultrasound system, Siemens Medical Solutions USA, Inc., whitepaper, 8 pp.

\* cited by examiner

METHOD AND APPARATUS FOR COMPOSITION OF ULTRASOUND IMAGES WITH INTEGRATION OF "THICK-SLICE" 3-DIMENSIONAL ULTRASOUND IMAGING ZONE(S) AND 2-DIMENSIONAL ULTRASOUND ZONE(S) UTILIZING A MULTI-ZONE, MULTI-FREQUENCY ULTRASOUND IMAGE RECONSTRUCTION SCHEME WITH SUB-ZONE BLENDING

TECHNICAL FIELD

The disclosed subject matter generally relates to systems and methods for ultrasound imaging, and more specifically to constructing a "thick-slice" image for any of the zones within a multi-zone, multi-frequency ultrasound imaging scheme using a 1.5 or 2 dimensional-array.

SUMMARY

For purposes of summarizing, certain aspects, advantages, and novel features have been described herein. It is to be understood that not all such advantages may be achieved in accordance with any one particular embodiment. Thus, the disclosed subject matter may be embodied or carried out in a manner that achieves or optimizes one advantage or group of advantages for ultrasound imaging without achieving all advantages as may be taught or suggested herein.

With the constant growth of the medical device industry, the demand for new medical devices that can process and provide useful insights regarding the collected data is also increasing. The ultrasound imaging systems and methods as described herein, can allow ultrasound imaging data be collected via a handheld ultrasound imaging device and displayed via a graphical user interface (GUI) on a user device.

The ultrasound systems and methods as described herein can provide also provide a "thick-slice" image for any of the zones within a multi-zone, multi-frequency ultrasound imaging scheme using a 1.5 or 2 dimensional-array. This imaging scheme that provides the ability to construct a "thick-slice" image for any of the zones within a multi-zone, multi-frequency ultrasound imaging scheme using a 1.5 or 2 dimensional-array. Upon receiving a user-input indicating to provide "thick-slice"/3D imaging for any zone of interest (if the returning energy of echoes to individual imaging rows is sufficient), the imaging process will construct a "thick-slice" image for that zone. In an example, a triple-zone system is imaged wherein zone1 can extend from an F# of 0 to 1, and zone2 from F# of 1 to 3, and zone3 from F# of 3 to 6. In this case, typically zone1 and/or zone2 can be "thick-slices" while the remainder zones can be typical 2-dimensional B-model image subsections. The "F#" refers to the f-number of the system, and relates to the ratio of the system's focal length f to the diameter d of the entrance pupil (sometimes referred to as the "clear aperture"). As one of skill in the art will appreciate, the F-number can affect the optics depth of field (DoF), e.g., the range between the nearest and farthest location where an object is acceptably in focus. An advantage of this imaging scheme is the ability to construct a "thick-slice" in the specific zone where a particular procedure might be getting performed (for example, a needle biopsy) or where a particular target of interest may reside that the practitioner may want a look at with multiple imaging slices. The entire image will be composited in the manners described hereinbelow. FIG. 1 illustrates examples of a composited image having a "thick-slice" image for any of the zones within a multi-zone, multi-frequency ultrasound imaging scheme using a 1.5 or 2 dimensional-array, according to various embodiments.

The ultrasound systems and methods as described herein can also provide a multi-zone (e.g., a triple-zone) multi-frequency, multi-imaging-modality scheme. An ultrasound system that implements a triple-zone embodiment utilizes an imaging method that includes three different depth zones with a certain transmit and receive beamforming scheme for each of the zones. The thickness or depth (e.g., as defined from a surface) can be different in various embodiments. For example, and as generally described in an example herein, in one embodiment a first zone ("zone1") can have a depth of from 0 to about 3.2 cm. A second zone ("zone2") can have a depth from about 3.2 cm to about 9.6 cm. A third zone ("zone3") can have a depth from about 9.6 cm to about 19.2 cm. In zone1 the system uses multi-angle plane-wave imaging. In zone2 the system uses focused transmits and Tissue Harmonic Imaging (THI) and can have a wide field-of view (FOV). In zone3 the system uses focused transmits and fundamental and subharmonic deep imaging. Using three different schemes for different depths to generate ultrasound images advantageously can reduce clutter and increase range. For example, in zone2 due to both the higher attenuation at greater depths, a desire to reduce clutter (e.g., due to fundamental frequency scattering) and utilize the range within which nonlinear propagation of ultrasound has a noticeable signature, zone2 utilizes THI and focused ultrasound transmissions. Different F#'s (focal length/diameter of the entrance pupil (effective aperture)) can also be used in each of the multiple zones. For example, ultrasound imaging in zone1 can utilize an F# of 0-1, ultrasound imaging in zone2 can utilize an F# of 1-3, and ultrasound imaging zone3 can utilize an F# of 3-6.

Another innovation is a thick slice 3D imaging involves using a 2-dimensional array in ultrasound systems which can presents a technical challenge in terms of the ability to simultaneously drive all of the elements, which requires a large number of drive channels, and to simultaneously receive from all of the elements, which requires a large number of receive channels. For ultraportable hand-held ultrasound systems, the ability to incorporate enough electronics either via dedicated chip design or off-the-shelf component use in a useable handheld device is a significant enough challenge. In embodiments of the invention of "thick-slice" 3D imaging, there are a few key ingredients that allow the entire system to be able to create a "thick-slice" image which is a 3-dimensional view of the medium underneath the array. During conventional 3D imaging the general expectation is that the transmitting and receiving ultrasonic array has elements in both its azimuth and elevation direction at a spacing typically in the range of half-wavelength of transmit frequency. If such an array were truly able to transmit across its 2-dimensions and had a matching number of coherent channels for both transmission and reception, it would lead to a 3-dimensional image (4-dimensional if including time as well). In embodiments of the invention, the methodology does not necessarily construct true 3D images in the conventional sense, but enables the ability to have multiple slices through the imaged medium. This provides the advantage of not needing to have the azimuth and elevational pitches be exactly the same.

Another innovation includes a method of generating a 3-dimensional (3D) image of a target area that includes multiple depth zones for acquiring data using a handheld ultrasound device, the method comprising imaging, using an ultrasonic array of the ultrasound device, a first zone by transmitting into the first zone and receiving ultrasound signals from the first zone using a multi-angle plane wave imaging scheme, the first zone having a depth dimension that extends from a surface of an object being imaged to a $1^{st}$ depth into the object; imaging, using the ultrasonic array, a second zone by transmitting into the second zone and receiving ultrasound signals from the second zone using a tissue harmonic imaging scheme, the second depth zone extending from the $1^{st}$ depth to a $2^{nd}$ depth into the object, the $2^{nd}$ depth being farther from the surface of the object than the $1^{st}$ depth, the first zone being between the second zone and the ultrasonic array, wherein imaging the first zone or the second zone includes forming a thick slice image of the first zone or the second zone, or imaging the first zone and the second zone includes forming a thick slice image of the first zone and the second zone; imaging, using the ultrasonic array, a third zone by transmitting into the third zone and receiving ultrasound signals from the third zone using fundamental and subharmonic deep imaging, the third zone extending from the $2^{nd}$ depth to a $3^{rd}$ depth farther from the surface of the object than the $2^{nd}$ depth, the second zone being between the first zone and the third zone; and forming a 3D image based on the received signals from the first zone, the second zone, and the third zone.

Various embodiments of such methods can include more, fewer, and/or different aspects. For example, in one embodiment, the $1^{st}$ depth is in the range of 0.0 cm to about 10 cm, wherein the $2^{nd}$ depth is in the range of 2 cm to about 18 cm, and wherein the $3^{rd}$ depth is in the range of 6 cm to about 18 cm. In some embodiments, a depth extent of the imaging of the first zone corresponds to a F# of 0 to about 1. In some embodiments, a depth extent of the imaging of the second zone corresponds to an F# of about 1 to about 3. In some embodiments, a depth extent of the imaging of the third zone corresponds to an F# of about 3 to about 6. In some embodiments, imaging the first zone further comprises accumulating signals from a plurality of angles of plane wave transmissions to coherently accumulate beamformed images, and forming a composite image from the accumulated signals. In some embodiments, accumulating signals for a plurality of angles of plane waves transmissions comprises accumulating signals for five or more different angles. In some embodiments, accumulating signals for a plurality of angles of plane waves transmissions comprises accumulating signals for nine or more different angles. In some embodiments, accumulating signals for a plurality of angles of plane waves transmissions comprises accumulating signals for 11 or more angles. In some embodiments, processing the signals received in the second zone using power pulse inversion processing. In some embodiments, imaging the third zone comprises utilizing focused transmits of ultrasounds signals, wherein the transmitted and received ultrasound signals are at the same frequency. In some embodiments, the method further comprises horizontally blending patches in the second zone and the third zone. In some embodiments, each patch in the second zone and each patch in the third zone has a height of the entirety of the respective zone. In some embodiments, horizontally blending patches comprises coherently summing respective phase and the amplitude information from neighboring patches for each pixel from respective receive beamforming for a pixel of its own patch and for any overlapping patches that may also contain said pixel. In some embodiments, the method further comprises vertically blending patches at interfaces between the first zone and the second zone, and the second zone and the third zone. In some embodiments, the array comprises four rows, each row having 128 elements. In some embodiments, method further comprises addressing each element of the array during imaging of the first zone, imaging the second zone, and imaging the third zone. In some embodiments, imaging the first zone includes employing a multiplexing scheme to simultaneously transmit ultrasonic signals from ultrasonic elements of the ultrasonic array that are positioned in the ultrasonic array in a same elevation direction. In some embodiments, imaging the first zone includes employing a multiplexing scheme to simultaneously transmit ultrasonic signals from ultrasonic elements of the ultrasonic array that are positioned in different rows of the ultrasonic array. In some embodiments, imaging the first zone includes employing a multiplexing scheme to transmit ultrasonic signals from each of a plurality of groups of ultrasonic elements of the ultrasonic array, each group of ultrasonic elements in a separate row of the ultrasonic array and positioned in a same elevation direction in the ultrasonic array, the multiplexing scheme driving each of the ultrasonic elements in a group to simultaneously transmit ultrasonic signals.

Another innovation includes a handheld ultrasound device, comprising a plurality of rows of ultrasonic elements, the rows arranged in parallel to form an array, the ultrasonic elements of the array characterized by an elevation pitch between ultrasonic elements in adjacent rows and an azimuth pitch between ultrasonic elements within the same row; a plurality of N-way multiplexers, each N-way multiplexor coupled to at least one element in each row; and a plurality of high-voltage pulsers configured to provide high voltage pulses to the ultrasonic elements the plurality of multiplexers; a plurality of analog front-end receivers coupled to the N-way multiplexers and configured to amplify and digitize received ultrasonic signals. The handheld ultrasound device an further include a control system coupled to the plurality of N-way multiplexers, the plurality of high-voltage pulsers, and the plurality of analog front-end receivers, the controls system operable for imaging, using the array, a first zone by transmitting and receiving ultrasound signals using a multi-angle plane wave imaging scheme, the first zone having a depth dimension that extends from a surface of an object being imaged to a $1^{st}$ depth into the object; and imaging, using the array, a second zone by transmitting and receiving ultrasound signals using a tissue harmonic imaging scheme, the second depth zone extending from the $1^{st}$ depth to a $2^{nd}$ depth into the object, the $2^{nd}$ depth being farther from the surface of the object than the $1^{st}$ depth, the first zone being between the second zone and the ultrasonic array, where imaging the first zone or the second zone includes forming a thick slice image of the first zone or the second zone, or imaging the first zone and the second zone includes forming a thick slice image of the first zone and the second zone. The controls system further operable for imaging, using the ultrasonic array, a third zone by transmitting and receiving ultrasound signals in the third zone using fundamental and subharmonic deep imaging, the third zone extending from the $2^{nd}$ depth to a $3^{rd}$ depth farther from the surface of the object than the $2^{nd}$ depth, the second zone being between the first zone and the third zone; and forming an image based on the received signals from the first zone, the second zone, and the third zone.

The details of one or more variations of the subject matter described herein are set forth in the accompanying drawings and the description below. Other features and advantages of the subject matter described herein will be apparent from the description and drawings, and from the claims. The disclosed subject matter is not, however, limited to any particular embodiment disclosed.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations as provided below.

The figures may not be to scale in absolute or comparative terms and are intended to be exemplary. The relative placement of features and elements may have been modified for the purpose of illustrative clarity. Where practical, the same or similar reference numbers denote the same or similar or equivalent structures, features, aspects, or elements, in accordance with one or more embodiments.

DETAILED DESCRIPTION OF CERTAIN INVENTIVE ASPECTS

In the following, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others. Although many of the examples relate to a handheld ultrasound device, the described systems and methods can also be incorporated into larger devices that are not necessarily handheld.

Figure 1:
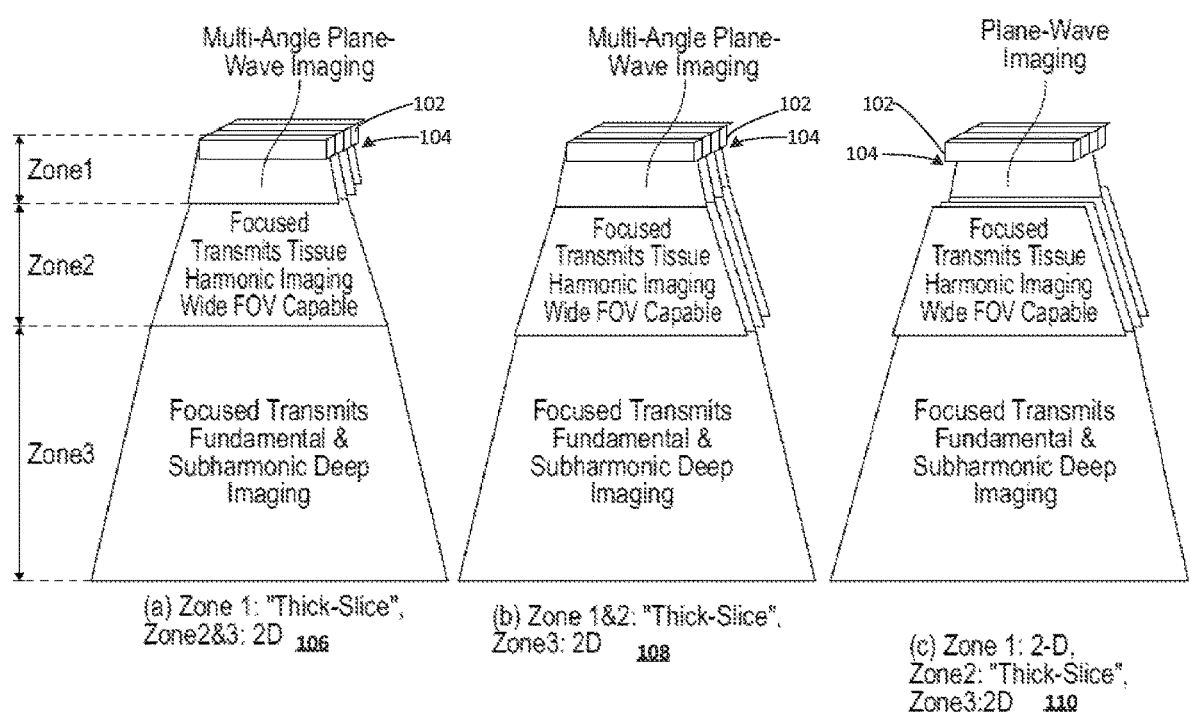
FIG. 1 illustrates an example of a representation of a "thick-slice" image for any of the zones within a multi-zone, multi-frequency ultrasound imaging scheme using a 1.5 or 2 dimensional-array. Upon user-request for "thick-slice"/3D imaging for any zone of interest, if the returning energy of echoes to individual imaging rows is sufficient, this invention will then construct a "thick-slice" image for that zone.

FIG. 1 illustrates an example of a representation of a "thick-slice" image for any of the zones within a multi-zone, multi-frequency ultrasound imaging scheme using a 1.5 or 2 dimensional-array 102. The location 104 represents a location where a proximal surface of an object, human, or animal (collectively referred to herein as an "object" for ease of reference), such that zone1, zone2, and zone 3 extend into the object. This imaging scheme can be used to construct a "thick-slice" image for any of the zones within a multi-zone, multi-frequency ultrasound imaging scheme using a 1.5 or 2 dimensional-array 102. Upon receiving a user-input to generate a "thick-slice"/three dimensional (3D) imaging for a zone of interest (if the returning energy of echoes to individual imaging rows is sufficient) this imaging scheme can construct a "thick-slice" image for that particular zone. In an example, in a triple-zone system where zone1 may extend from an F# of 0 to 1, zone2 from an F# of 1 to 3, and zone3 from an F# of 3 to 6, and zone1 and/or zone2 can be "thick-slices" while the remainder zones (e.g., zone3) can be a 2-dimensional (2D) B-model image subsections. One advantage of this imaging scheme is that it provides the ability to construct a "thick-slice" image in the specific zone where a particular procedure might be getting performed (for example, a needle biopsy) or where a particular target of interest may reside that the practitioner may want a look at with multiple imaging slices. In other words, a target location at a particular depth into an object that a particular procedure may be performed may correspond to zone1, zone2, or zone3, and for that zone the imaging scheme can construct a "thick-slice" image which when viewed provides more information about objects in the target location.

A graphic description of what such a composited image may look like is shown in FIG. 1. On the left side 106 of FIG. 1, (a) depicts an embodiment where it is desired to construct a "thick slice" image in zone1 and a 2D image in zone2 and zone3. This is done using ultrasonic imaging of zone1 with multi-angle plane wave imaging to create the "thick slice" image n zone1. Ultrasonic imaging of zone2 uses focused transmits and tissue harmonic imaging methodology. Ultrasonic imaging of zone3 uses focused transmits, using fundamental and subharmonic deep imaging to create a 2D image. In the center 108 of FIG. 1, (b) depicts an embodiment where it is desired to construct a "thick slice" image in zone1 and zone2, and a 2D image zone3. This can be done using ultrasonic imaging of zone1 using multi-angle plane wave imaging to create the "thick slice" image. Ultrasonic imaging of zone2 creates a thick slice using focused transmits and tissue harmonic imaging methodology. Ultrasonic imaging of zone3 uses focused transmits, using fundamental and subharmonic deep imaging to create a 2D image. In the right side 110 of FIG. 1, (c) depicts an embodiment where it is desired to construct a "thick slice" image in zone2 and a 2D image in zone1 and zone3. This can be done using ultrasonic imaging of zone1 using plane wave imaging. Ultrasonic imaging of zone2 creates a 2D image using focused transmits and tissue harmonic imaging methodology. Ultrasonic imaging of zone3 uses focused transmits, using fundamental and subharmonic deep imaging to create a 2D image. The entire image can be composited in the manners described below in reference to FIGS. 2-12.

Figure 2:
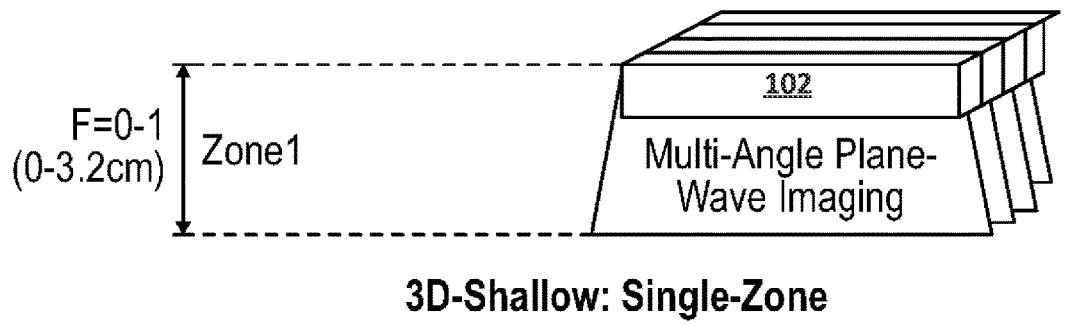
FIG. 2 illustrates an example of a representation of "thick-slice" 3-dimensional (3D) ultrasound imaging technology utilizing a multi-zone, multi-frequency ultrasound image reconstruction scheme with sub-zone blending.
Figure 2:
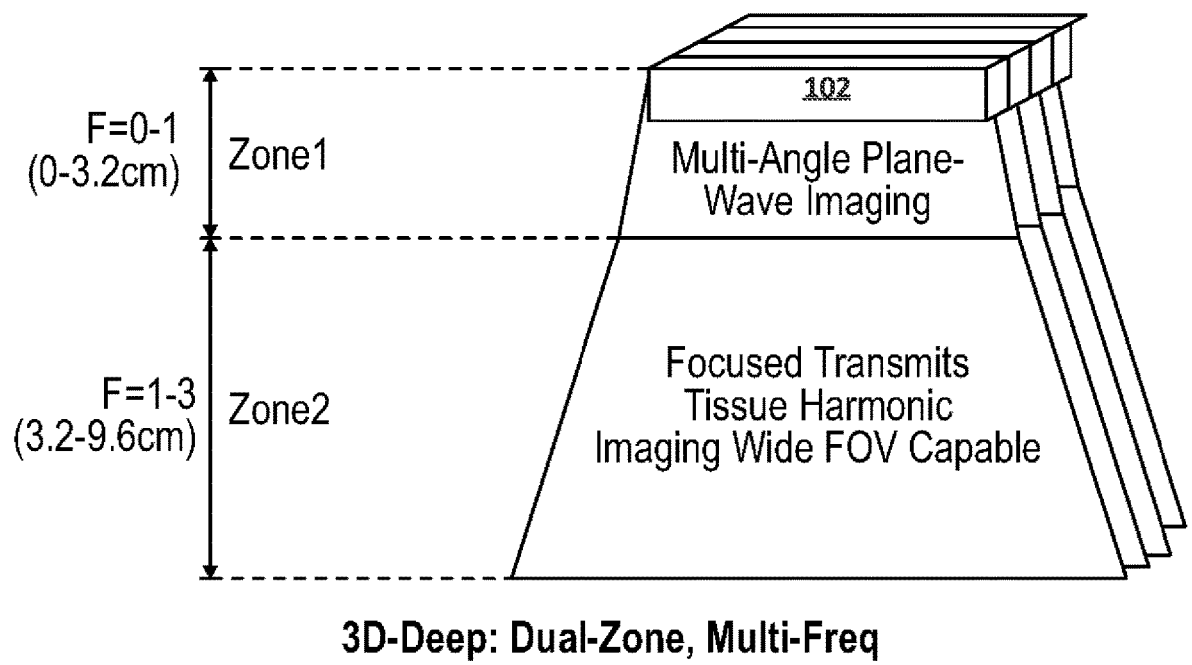
Figure 3:
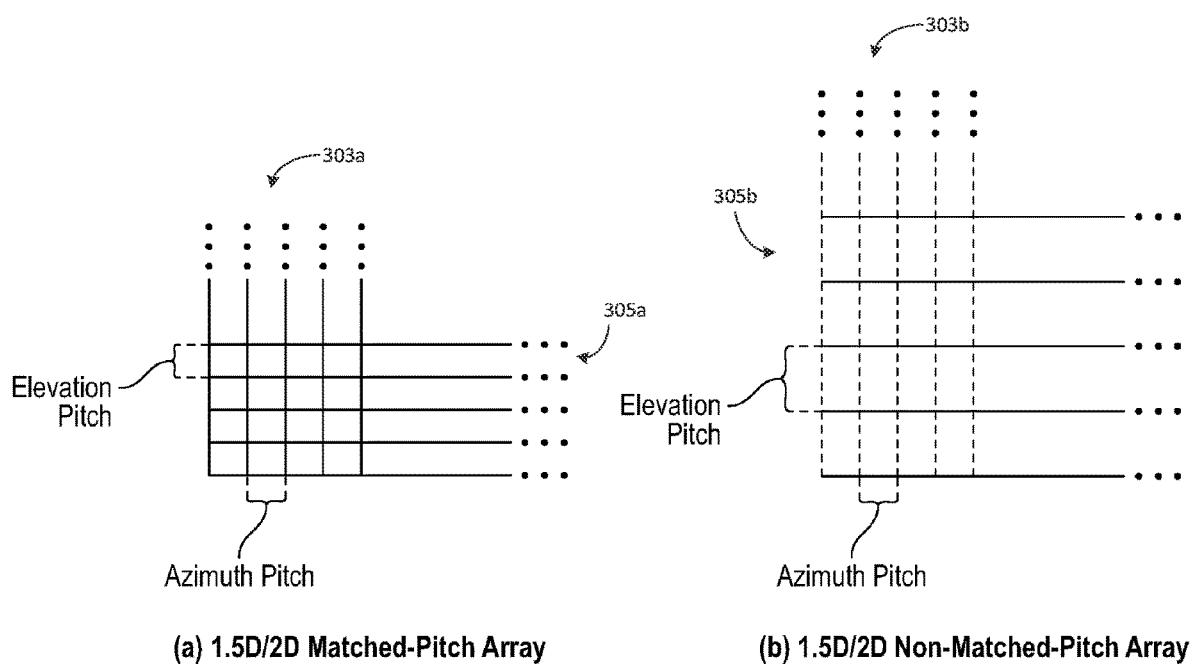
FIG. 3 illustrates examples of elevation and azimuth pitches in an ultrasonic array, where an ultrasonic array having elements in both its azimuth and elevation direction at a spacing typically in the range of half-wavelength of transmit frequency is depicted in FIG. 3(a), and an ultrasonic array having elements where the azimuth and elevation pitches are not (exactly) the same, depicted in FIG. 3(b).

FIG. 2 illustrates an example of a representation of "thick-slice" 3-dimensional (3D) ultrasound imaging technology utilizing a multi-zone, multi-frequency ultrasound image reconstruction scheme with sub-zone blending. "Thick-slice" 3D imaging is a three-dimensional imaging scheme using a 2D array 112. Using a 2D array 112 in an ultrasound systems for the imaging scheme presents a difficult technical challenge in terms of the ability to simultaneously drive all of the elements of the array, which requires a large number of drive channels, and to simultaneously receive from all of the elements, which requires a large number of receive channels. For ultraportable hand-held ultrasound systems, the ability to cram enough electronics, either via dedicated chip design or off-the-shelf components, is a significant barrier to such implementations. In embodiments of a "thick-slice" 3D imaging, there are a few key ingredients that allow the entire system to be able to create a "thick-slice" image which is a 3-dimensional view of the medium underneath the array. Key features of the invention will be described below.

A. Concept: "Thick-slice" 3D imaging is a concept that's related to, but not exactly the same as conventional 3D imaging. During conventional 3D imaging the general expectation is that the transmitting and receiving ultrasonic array has elements in both its azimuth and elevation direction at a spacing typically in the range of half-wavelength of a transmit frequency. If such an array were truly able to transmit across its 2-dimensions and had a matching number of coherent channels for both transmission and reception, it would lead to a 3-dimensional image (4-dimensional, if including time as well). Typically, such an array with elevation pitch and azimuth pitch being the same would pictorially be represented as shown in FIG. 3(a), where the elevation pitch of elements (e.g., ultrasound transducers) in rows 305a of the array is the same as the azimuth pitch of the elements in columns 303a of an array. For embodiments of this invention, the intent is not necessarily to construct true 3D images in the conventional sense, but to enable the ability to have multiple slices through the imaged medium. This opens up the possibility of not needing to have the azimuth and elevational pitches be exactly the same, as shown in FIG. 3(b), which illustrates an elevation pitch of elements in rows 305b of an array is the different than an azimuth pitch of the elements in columns 303b of the array. Note that the implementation illustrated in FIG. 3(b) does not preclude FIG. 3(a) as a subset of it.

B. Pitch considerations for "thick-slice" imaging: There are some key advantages to increasing the elevational pitch:
  (i) increased yield in most manufacturing processes (wherein the increase in yield can be dependent on actual dimensions of the array);
  (ii) increased transmit amplitude leading to deeper sound penetration for deeper imaging and increased receive amplitude leading to higher received signal levels; and
  (iii) increased natural focal depth for each element, which enables deeper imaging by bringing the beam to a narrower diameter deeper into the medium.

The primary determinant for azimuth pitch will continue to be the key transmit and receive frequencies of interest, within the bandwidth that would be characteristic of the ultrasonic array material and the dimensions of each element (which would refer to both the active element area and the spacing (kerf) between adjacent elements).

In various embodiments of this invention, a succession of 2-dimensional B-mode acquisitions are completed and then beamformed.

FIG. 2 illustrates two different types of "3D" (more appropriately "thick-slice") imaging designed to handle both shallow and medium depth ultrasound imaging. They would consist of zone 1 only for shallow thick-slice imaging. For relatively deeper thick-slice imaging they would consist of zone1 and zone2. The entire sequence of zone1 and zone2 imaging would proceed forward with Transmit, Receive and then beamforming in accordance with the methods described herein. Importantly, in addition to the set of 2D frames that comprise a 'thick-slice' this invention also contemplates the beamforming computation of some interpolated frames (see section C. Interpolated Frames below).

C. Interpolated frames: coherent and/or alpha-blended. It is important to keep in mind that in addition to the set of 2D frames as shown in FIG. 2, this invention also contemplates:
  a. The beamforming computation of in-between frames within a few wavelengths of each computed 2-dimensional frame.
  b. Pixel-interpolated in-between frames 404 which would allow for the 'thick-slice' to have more 2-dimensional frames than just the frames 402 directly underneath each row of elements of the ultrasonic array 102. The interpolated frames 404 can This may be seen in FIG. 4. The directly imaged 2D image frames 402 are depicted in white while the interpolated frames 404 are shown in a darker gray. The interpolated frames 404 can be generated by, for example, linearly averaging the frames 402 on either side of each interpolated frame, or by using another interpolation technique (e.g., a non-linear interpolation process including but not limited to polynomial interpolation, spline interpolation, or interpolation using Gaussian process).

Figure 5:
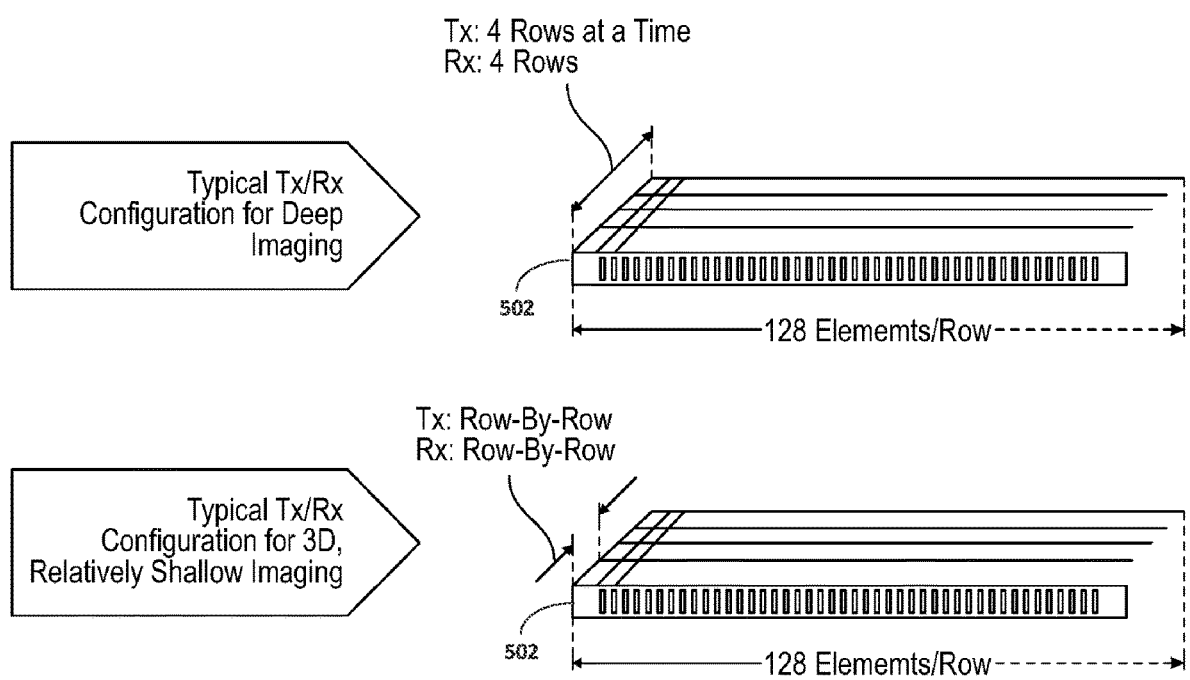
FIG. 5 illustrates an example array structure and multiplexing for a 1.5D array.

D. Advanced element to channel multiplexing scheme for deep 2D and shallow/medium 'thick-slice' imaging using a single 1.5D array: The ability to take an array with a larger number of elements than the actual number of coherent channels for transmitting or receiving is typically enabled by a 'multiplexer' which is essentially a signal-router that may select a subset of the larger number of elements to either transmit from or receive from.

a. Ultrasonic Array description: Typically, a "1.5D" array, where the number of elements in elevation direction (e.g., the number of rows) is noticeably lower than the number of elements in azimuth direction (e.g., the number of elements in a row), is setup such that not every element is individually addressable. It's also more typical for equidistant rows on either side of a central row to fire together in such cases. The intended use in such scenarios is to improve the elevational focus of the transmitted beam, typically at some focal point that would correspond with the focal length target of the lens itself. The designs of ultrasound devices described herein are not constructed or operated with the limitations of not being able to address every element and are not required to have rows equidistant from a central row transmit together. Instead, these devices leverage the ability to address each element in each row separately to instead construct a "thick-slice" image of a target zone.

b. Array structure and Multiplexing for 1.5D array: The ability to be able to produce both 2D images (shallow through deep) and 3D images (shallow through medium depth) relies on a particular design scheme for the ultrasonic array and the 'multiplexing'-scheme for drivers/receivers in terms of how they may address each element of the ultrasonic array. The fundamental idea is the existence of a 1.5D ultrasonic array and a multiplexing-scheme that allows each ultrasonic element to individually be selectable such that (a) all elements in 'elevation' direction may fire together effectively giving an ultrasonic array whose elements are as wide as there are number of rows in the array (b) all elements in 'elevation' direction may fire separately effectively giving an ultrasonic array that can do 3-dimensional imaging. In a particular example of an array within the described systems, the array includes 128 elements in 4 rows, though other such arrangements may also be constructed. A feature of these arrays can be a '1.5D' array where # of elements along the 'elevation' direction is usually substantially smaller than the # of elements in the 'azimuth' direction (in this case 4 rows and 128 elements/row respectively). FIG. 5 illustrates an example array structure and multiplexing for a 1.5D array 502, according to some embodiments. In addition, there can also be other schemes for both Transmitting and Receiving configurations that can be constructed using this 1.5D ultrasonic array 502 that can lend themselves to various flavors of 'Synthetic Aperture'-based ultrasound image acquisition and reconstruction.

c. Multiplexing Schemes: As noted in section b above, the existence of a sophisticated multiplexing scheme is integral to enabling the various imaging modes described in the multiple inventions noted in this disclosure. While the concept of signal multiplexing to map to a finite (and lower) number of channels is not new, this section is included here so that the underlying enabling design considerations are understood.

Figure 6:
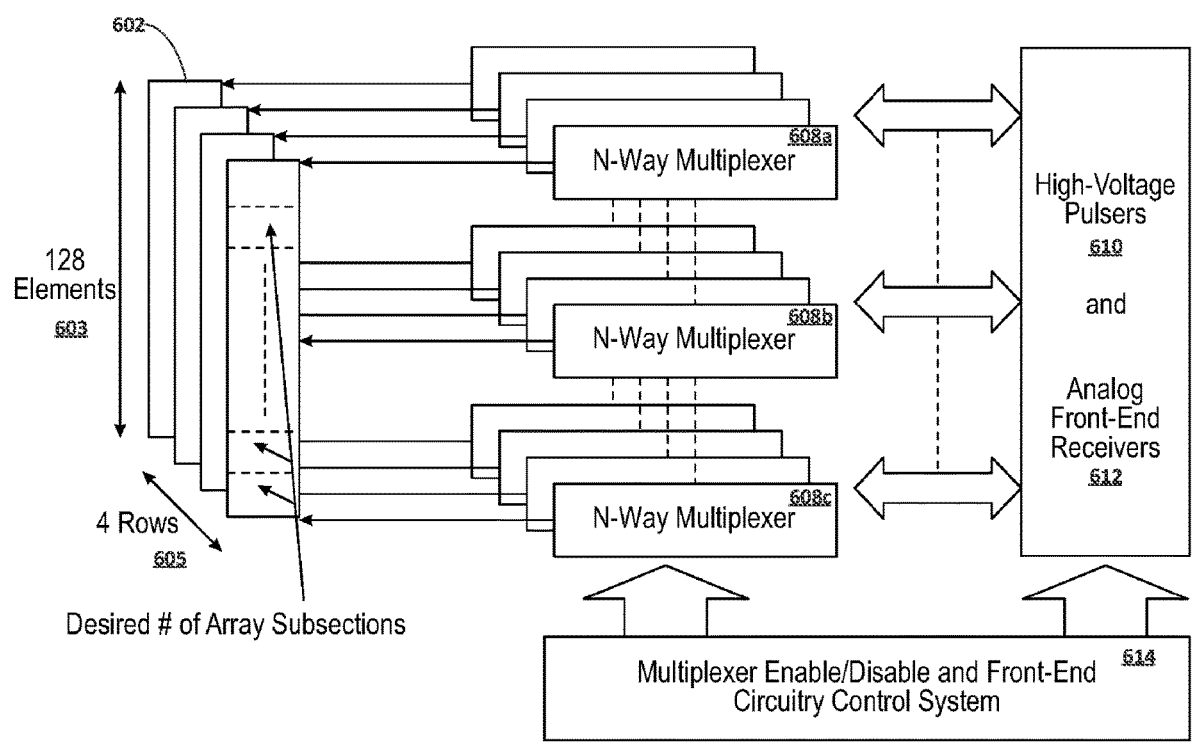
FIG. 6 illustrates an example of a representation of a general scheme to be able to access each element or set of elements of interest in a manner so as to enable various imaging aspects described herein, here showing 4 rows of 128 ultrasonic elements each, where the elements in are all addressable for both transmit and receive.

An example of a general scheme that's needed to be able to access each element or set of elements of interest in a manner so as to enable various imaging aspects of inventions noted herein is illustrated in FIG. 6, showing an array 602 having four rows of 128 ultrasonic elements each, where the elements in each of the four rows are all addressable for both transmit and receive. On the left are four rows 604 of 128 ultrasonic elements 602 each. Nothing in this invention disclosure limits it to four rows or to 128 elements per row. Instead, embodiment can have a number of rows of elements that are all addressable for both transmitting ultrasound signals and receiving ultrasound signals (reflections of the transmitted ultrasound signals propagating back through a zone after reflecting off of one or more objects). The dashed lines within each row of ultrasonic elements refers to desired number of subsections within each row, wherein each subsection may have multiple individual ultrasonic elements contained within it.

To the right of it are the N-way multiplexers 608. Each of these multiplexers 608 may be capable of directly addressing a certain number of elements 603 by virtue of how many "channels" each multiplexer can support (8 or 16 or 32 or 64 for example). This number of elements 603 will typically determine what the number of individual ultrasonic elements 603 within each subsection of each row 605 will end up being set to. Typically, the number of ultrasonic elements 603 within each section corresponds to the number of channels that a multiplexer 608 can support. except in the case of relatively weaker electromechanical conversion efficiency ultrasonic elements 603 for either/both transmit and receive, in which case several of those ultrasonic elements 603 may be tied together to a single channel. This latter case tends to appear in the case of micromachined ultrasonic transducers for either/both transmit and receive cases.

In addition to the ultrasonic array of elements 603 and the multiplexers 608, there are also the High-Voltage pulsers 610 (which may typically have the Transmit/Receive directionality switch contained within them), and analog front-end receivers 612 (these amplify and digitize the received echoes as their primary task), in communication with the multiplexers 608. A multiplexer enable/disable and front-end circuitry control system 614 can be used to control the operation of the system. For example, controlling of the N-Way Multiplexers 608 to transmits and receive ultrasonic signals via the array 602.

The presence of the above multiplexing scheme allows this invention the capability to: (a) short respective elements within each row and fire them together for transmit and/or receive from them together/individually (b) be able to address each row individually for both transmitting and receiving. These various transmit and receive modalities are described in herein.

Figure 7:
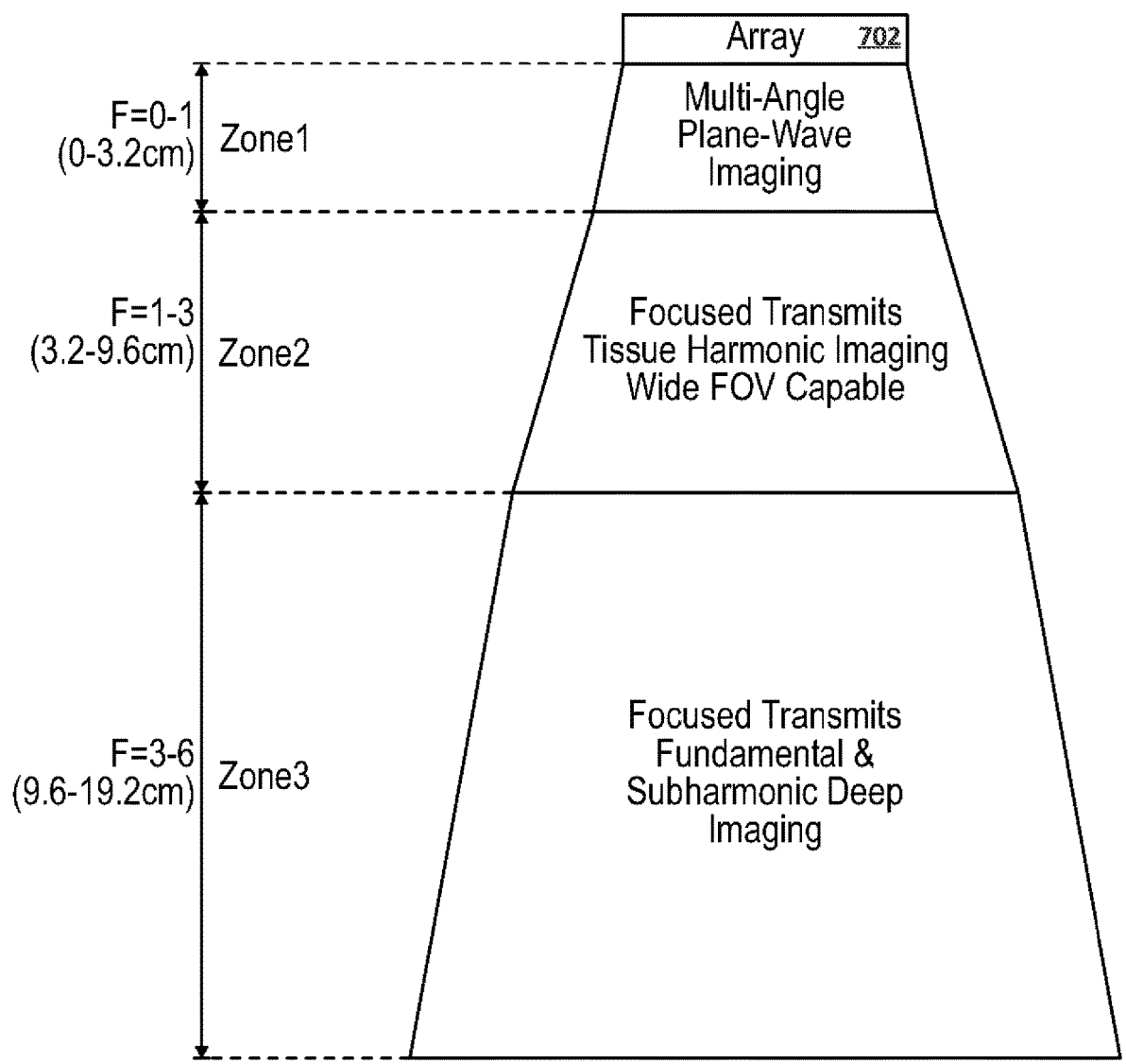
FIG. 7 illustrates an example of a triple-zone, multi-frequency image reconstruction scheme.
Figure 8:
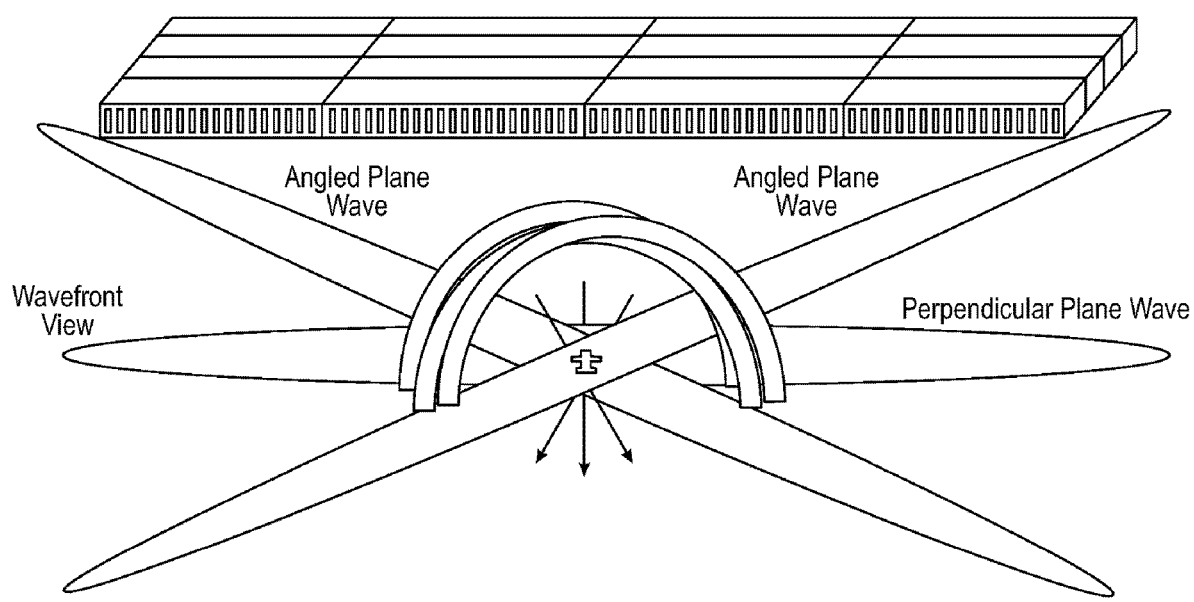
FIG. 8 illustrates an example of a pictorial representation of transmitting plane waves at three angles into a medium for a plane wave imaging zone.

FIG. 7 illustrates an example of a triple-zone, multi-frequency image reconstruction scheme in accordance with certain aspects of this invention. More specifically, FIG. 7 illustrates an array 702 that can be positioned near the surface of an object to collect ultrasound data, and depicts a representation of a triple-zone, multi-frequency, multi-imaging-modality method that can be used in a handheld ultrasound device. The "object" can be, for example, a human, any type of animal (e.g., a horse, a dog, and the like) or another type of object that has a depth dimension that may benefit from this method of imaging. In some embodiments, the F# for zone1 can be greater than 1, for example, 1.1, 1.2. 1.3, 1.4, 1.5, or greater. Generally, the F# for zone1 is less than the F# for zone2, which is less than the F# for zone3. The depth, or thickness of each zone can vary with implementation, and may be based on the nature of the object being imaged. For example, how the material comprising the object attenuates ultrasonic waves, or where a particular target of interest in the object is located. In some embodiments, the first zone can extend from the surface of the object being imaged to a $1^{st}$ depth such that the first zone has a certain thickness (e.g., 2.5 cm-4.5 cm), the second zone can extend from the $1^{st}$ depth to a $2^{nd}$ depth, and the third zone can extend from the $2^{nd}$ depth to a third depth. In some embodiments, the first and second zone can overlap, and the second and third zone can overlap—such embodiments may help generate additional data in the area of the transition from one zone to another which may help improve images that are generated that include the boundary regions of the first zone to the second zone and/or the second zone to the third zone. The depth of each zone can be dependent on the full aperture of the ultrasonic array being used. Various embodiments may use arrays having a different number or rows, a different number of elements in each row, and a different elevation and azimuth pitch of the array. In some embodiments, the $1^{st}$ depth may be in the range of 0.0 cm (e.g., on or adjacent to the surface of object) to about 10 cm, the $2^{nd}$ depth may be in the range of 2 cm to about 18 cm, and the $3^{rd}$ depth may be in the range of 6 cm to about 18 cm. In the example illustrated in FIG. 7, the F# of zone1 is 0-1, the F# of zone2 is 1-3, and the F# or zone3 is 3-6. In this example, the depth of zone1 can be in the range of 0 (e.g., the surface of the object being imaged) to about 3.2 cm, the depth of zone2 can be in the range of about 3.2 cm to about 9.6 cm, and the depth of zone3 can be in the range of about 9.6 to about 19.2 cm. In some embodiments, the $1^{st}$ depth extends a distance from the array of, for example, 0.0, 0.1, 0.2, 0.3. 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.4, 2.6, 2.7, 2.8, 2.9, 3.0, 3.1, or 3.2 cm, plus or minus 0.05 cm, e.g., from the array. In some embodiments, the $2^{nd}$ depth extends a distance from the array of, for example, 2.0. 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.8, 10.9, 11.0, 11.1, 11.2, or 11.3 cm, plus or minus 0.05 cm. In some embodiments, the $3^{rd}$ depth extends a distance from the array of, for example, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.8, 10.9, 11.0, 11.0, 11.1, 11.2, 11.3, 11.4, 11.5, 11.6, 11.7, 11.8, 11.9, 12.0, 12.1, 12.2, 12.3, 12.4, 12.4, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20 cm, plus or minus 0.05 cm. Although in various other examples, the depth of zone1, zone2, and zone3 can be different, for certain preferred embodiments the starting and ending depths of the zones are within the ranges shown in FIG. 7. As described in more detail below, FIG. 7 illustrates a process of ultrasound imaging where data is collected in each of three "vertical" zones (corresponding to different depths of imaging) using a different process. For example, in zone1 data is collected using multi-angle plane-wave imaging. In zone2, data is collected using focused transmissions and tissue harmonic imaging. In zone3 data is collected using focused transmissions and fundamental and subharmonic deep imaging. The data is collected in all three zones using an array that is configured such that each element of the array is individually addressable. In some embodiments, the array has four rows of 128 elements, although other configurations are also possible.

E. Image Reconstruction for each frame within a thick slice a. Triple-zone Concept: The triple-zone concept is one example of a multi-zone imaging scheme that can utilize three different depth zones, and with different transmit and receive beamforming schemes in each zone.

(i) Zone1: (PWI-zone): This zone would typically be within an F# of 0 to about 1. Due to being primarily in the near-field, zone1 will be imaged using 'Plane Wave Imaging' (PWI). In addition to PWI, this near-zone benefits from the ability to be imaged at high-frequency since the overall attenuation within the imaged medium for a given frequency and depth extent for zone1 can be set to the lower of dB gain in receive system and an F# limit (in this case 1). A number of angles of plane wave transmission (11 for example) would be used to then coherently accumulate their received beamformed images and composite a high-resolution image for this zone.

(ii) Zone2: (THI-zone): This zone would typically be within a depth extent corresponding to an F# of 1 through 3. It would utilize Tissue Harmonic Imaging (THI). As before, this depth extent can be set based on the expected attenuation for roundtrip of fundamental transmit frequency and received harmonic frequency. A robust Power-pulse inversion (PPINV) method would be used for receiving the generated harmonics due to the nonlinear propagation of ultrasound in organic tissue. Due to both the depth (leading to higher attenuation) and desire to reduce clutter (due to fundamental frequency scattering) and the range within which nonlinear propagation of ultrasound has a noticeable signature, this zone will utilize THI and focused transmissions. The number of focused transmissions would depend on the transmitted frequency, zone illumination target and achievable resolution. For the example shown, at a focal radius of −6.4 cm, a typical separation of the focal points would be approximately 2 mm at a transmitted frequency of 2.5 MHz and with an array aperture of roughly 3.2 cm consisting of 128 elements in the azimuth direction. Additionally, the number of focal points would also be determined by the angle of Field of View (FOV). For example, a wider field of view (more common) would lead to a wider "sector" image with larger number of focused transmissions, while a narrower field of view (not common) will lead to lesser number of focused transmissions. Typically, the FOV doesn't exceed roughly 45° subtended at the center of the transmitting array.

(iii) Zone3: (fundamental-zone): This zone would typically be within a depth extent corresponding to an F# of 3 through 6. It would utilize Focused Transmits similar to in zone2, but instead of THI, both the transmit and receive would be at the transmitted frequency itself. As before, this depth extent can be set based on the expected attenuation for roundtrip of ultrasound under typical attenuation assumptions. The number of focused transmissions would depend on the transmitted frequency, zone illumination target and achievable resolution. For the example shown, at a focal radius of −14 cm, a typical separation of the focal points would be approximately 2 mm at a transmitted frequency of 2.5 MHz and with an array aperture of roughly 3.2 cm consisting of 128 elements in the azimuth direction. Note that the full-width at half-maximum (FWHM) will likely be larger than 2 mm (for the example shown) because of distance from the array. However typically at this depth the granularity of focused transmissions needs to remain fine (or be finer) to get enough illumination into this deep zone. Additionally, the number of focal points would also be determined by the angle of Field of View (FOV). For example, a wider field of view (more common) would lead to a wider "sector" image with larger # of focused transmissions, while a narrower field of view (not common) will lead to lesser number of focused transmissions. Typically, the FOV doesn't exceed roughly 45° subtended at the center of the transmitting array.

b. Beamforming:

(i) Zone1: Zone1 is a PWI-zone. Within this zone, the Transmitted waves will be sent in an unfocused (or far-focused) manner. The received waves will be focused at every point. Receive beamforming will be done by calculating roundtrip delay information for each pixel to every element in the aperture.

1. Intermediate vertical scan lines: Depending on the ratio of transmitted wavelength to the azimuthal separation between elements in the array, there may or may not be intermediate vertical scan-lines computed during images reconstruction in addition to the lines that have timeseries information for each of the receiving elements. The presence of these lines depends on whether there's enough coherent delay and phase information to create pixels with useful information content along these intermediate vertical lines.

2. Receive Aperture: A further enhancement to Receive beamforming is to apply an adjustable aperture that's correct for every pixel for which beamforming is being done.

3. Receive Apodization: A further enhancement is to also apply an apodization during Receive beamforming to further improve the quality of the reconstructed image.

4. Transmit Apodization: Yet another enhancement to this method is to apply an apodization also to the transmitted "Plane Wave" by shaping the transmitted waveform during transmit so that the overall plane wave has the desired transmit wavefront amplitude shape.

5. Receive Beamforming for Angled Transmissions: For this 'Plane Wave' imaging zone, there'll be a sequence of image acquisitions that'll be done by transmitting these Plane Waves at various angles into the medium and beamforming the received waveforms for each of those cases. A pictorial representation of three such angles is shown below in FIG. 8, which illustrates an example of transmitting plane waves at three angles into a medium for a plane wave imaging zone. In various embodiments, the reconstructed image for each angled transmission can be coherently summed (with phase and amplitude information) or summed up after the pixel intensity has been computed. The implementation choice between these two methods can be dependent on various factors such as the frequency, angle of transmission, etc., which can determine whether coherent summation leads to useful information content in a reconstructed image. The number of angles will be limited by the granularity with which the hardware can transmit them, the overall acquisition time (which would depend on the roundtrip time within the maximum extent allowable for zone1), and also any computational limits of associated hardware for beamforming. It'll typically span the range of interest expected to yield enough clutter reduction in the reconstructed image within this zone. For the example shown in FIG. 8, the total number of anticipated angles for Plane Wave imaging within zone1 is 11, at a granularity of −2°, hence covering the span from −10° through +10°. For ultrasound-guided needle procedures a few relatively steep angles (up to 45° or so) may be included in the mix to attempt to get signal from needles that may be at steeper angles of ingress.

6. Time-averaging: Another method that may be used for enhancing the quality of image is dependent on the speed with which images can be reconstructed within this zone. Since this zone is expected to be shallow, the Transmit+Receive round-trip time is not expected to be large. In addition, beamforming within this zone will be relatively faster due to reduced number of pixels. Therefore, in addition to the opportunity to add more angled transmissions, this zone will also be able to benefit from the time-averaging of images collected over a relatively short period of time (e.g., less than a second). For example, time-averaging of images accumulated over a few milliseconds.

(iii) Zone2: Zone2 is a THI-zone. Within this zone, the Transmitted waves will be sent in a focused manner to the number of focal points appropriate to the field of view and frequency of transmission. The received waves will be focused at every point in the reconstructed image for Zone2. Receive beamforming will be done by calculating roundtrip delay information for each pixel to every element in the aperture. This zone will utilize a method of Tissue Harmonic imaging that's commonly known as Power Pulse Inversion Imaging (PPINV). The intrinsic advantages of tissue harmonic imaging are superior definition of tissue and boundaries while leading to a reduction of speckle artifacts. PPINV-based THI method(s) utilize the advantage of deeper penetration at lower transmission frequencies. However, other methods for THI that may utilize bandpass filtering upon receive—or—phase cancellation—or—encoding—or—other pulse inversion techniques may also be utilized in this zone.

1. Intermediate vertical scan lines: Depending on the ratio of transmitted wavelength to the azimuthal separation between elements in the array, there may or may not be intermediate vertical scan-lines computed during images reconstruction in addition to the lines that have timeseries information for each of the receiving elements. The presence of these lines depends on whether there's enough coherent delay and phase information to create pixels with useful information content along these intermediate vertical lines.

2. Patch beamforming: Within this zone since each focused transmit event targets a particular focal point, it'd stand to reason then that Receive beamforming be carried out in a near region ('Patch') of that focal transmission point. The particular schemes and methods of patch beamforming and patch-blending are explained in the Image Compositing section (Section A→c)

3. Receive Aperture: A further enhancement to Receive beamforming is to apply an adjustable Receive aperture that's correct for every pixel for which beamforming is being done. In typical use, since Zone2 is expected to span a range beyond a F-number of 1 (YL's design for instance will target F-number of 1 till 3 for Zone2), the entire lens aperture may be in use.

4. Transmit Aperture: A further enhancement to Transmit beamforming is to apply an adjustable aperture that's appropriate to each sub-zone within this zone. This aperture may be made proportional to the F-number so that it (the aperture) gets larger for deeper imaging (to compensate for attenuation) and slides across the full lens aperture until it attains full coverage for all cases at a particular depth. For points that are deeper than that, the Transmit aperture will equal the intrinsic lens aperture itself. The intent behind using reduced transmit aperture for shallower points within Zone 2 also has to do with not insonifying parts of the imaged medium for which beamforming will not be done but they may still contribute to reverberation and other artifacts via refraction into the area of interest for which beamforming will be done. By reducing or minimizing transmitted waveforms in the shallower portions of Zone2 unwanted reverberations and/or artifacts can also be reduced or minimized.

5. Receive Apodization: A further enhancement is to also apply an apodization during Receive beamforming to further improve the quality of the reconstructed image.

6. Transmit Apodization: Yet another enhancement to this method is to apply an apodization also to the transmitted wave by shaping the transmitted waveform during transmit so that the overall focused wavefront has the desired transmit amplitude shape from one end to the other of the transmitting aperture.

7. Time-averaging: Another method that may be used for enhancing the quality of image is dependent on the speed with which images can be reconstructed within this zone. In scenarios where the boundaries defining the start and end of zone 2 are relatively shallow (but not completely encompassing zone1), the Transmit+Receive round-trip time may end up being not large. In addition, beamforming within this zone in cases where the start and end depths defining zone 2 are shallow, the overall beamforming computations will be relatively faster due to reduced number of pixels. Therefore, in addition to the opportunity to add more focused transmissions for better illumination, or the opportunity to deploy alternate methods of tissue inversion, this zone will also be able to benefit from the time-averaging of images accumulated over a few milliseconds.

(iii) Zone3: Zone3 is a fundamental frequency-zone. Within this zone, the Transmitted waves will be sent in a focused manner to the number of focal points appropriate to the field of view and frequency of transmission. The received waves will be focused at every point in the reconstructed image for Zone3. Receive beamforming will be done by calculating roundtrip delay information for each pixel to every element in the aperture.

1. Intermediate vertical scan lines: Depending on the ratio of transmitted wavelength to the azimuthal separation between elements in the array, there may or may not be intermediate vertical scan-lines computed during images reconstruction in addition to the lines that have timeseries information for each of the receiving elements. The presence of these lines depends on whether there's enough coherent delay and phase information to create pixels with useful information content along these intermediate vertical lines. In typical use these additional vertical scan lines may NOT be there since zone3 will typically be deep enough that at typical transmission frequencies suited to such depths the Full-Width-At-Half Maximum (FWHM) beam diameter might be large enough that interpolated scan lines may not be useful.

2. Patch beamforming: Within this zone since each focused transmit event targets a particular focal point, it'd stand to reason then that Receive beamforming be carried out in a near region ('Patch') of that focal transmission point. The particular schemes and methods of patch beamforming and patch-blending are explained in the Image Compositing section (Section A→c).

3. Receive Aperture: A further enhancement to Receive beamforming is to apply an adjustable Receive aperture that's correct for every pixel for which beamforming is being done. In typical use, for deep imaging with Zone3, the entire lens aperture may be in use.

4. Transmit Aperture: A further enhancement to Transmit beamforming is to apply an adjustable aperture that's appropriate to each sub-zone within this zone. This aperture may be made proportional to the F-number so that it grows for deeper imaging (to compensate for attenuation) and slides across the full lens aperture until it attains full coverage for all cases at a particular depth. For points that are deeper than that, the Transmit aperture will equal the intrinsic lens aperture itself. The intent behind using reduced transmit aperture for shallower points within Zone 3 also has to do with not insonifying parts of the imaged medium for which beamforming will not be done but they may still contribute to reverberation and other artifacts via refraction into the area of interest for which beamforming will be done. In typical use, for deep imaging with Zone3, the entire lens aperture will be in use.

5. Receive Apodization: A further enhancement is to also apply an apodization during receive beamforming to further improve the quality of the reconstructed image.

6. Transmit Apodization: Yet another enhancement to this method is to apply an apodization also to the transmitted wave by shaping the transmitted waveform during transmit so that the overall focused wavefront has the desired transmit amplitude shape from one end to the other of the transmitting aperture.

7. Time-averaging: Another method that may be used for enhancing the quality of image is dependent on the speed with which images can be reconstructed within this zone. In scenarios where the boundaries defining the start and end of zone 3 are relatively shallow (but not completely encompassing zone1 and/or zone2), the Transmit+Receive round-trip time may end up being not large. In addition, beamforming within this zone in cases where the start and end depths defining zone 3 are relatively shallow, the overall beamforming computations will be relatively faster due to reduced number of pixels. Therefore, in addition to the opportunity to add more focused transmissions for better illumination, or the opportunity to deploy alternate methods of tissue inversion, this zone may also be able to benefit from the time-averaging of images accumulated over a few ms. In typical use scenarios however this will not be the case since zone3 is targeted toward deep imaging and hence by definition will likely not be able to benefit from this.

8. Subharmonic THI-based image quality enhancement: Zone3 may also lend itself to the ability to deploy subharmonic imaging wherein lower frequency harmonic components are computed to get better resolution at higher depths. In such cases, this zone may utilize a method of Tissue Harmonic imaging that's commonly known as Power Pulse Inversion Imaging (PPINV). The intrinsic advantages of tissue harmonic imaging are superior definition of tissue and boundaries while leading to a reduction of speckle artifacts. PPINV-based THI method(s) utilize the advantage of deeper penetration at lower transmission frequencies. However, other methods for THI that may utilize bandpass filtering upon receive—or—phase cancellation—or—encoding—or—other pulse inversion techniques may also be utilized in this zone.

c. Image Compositing:

(i). Beamforming patches: zone2 and zone3: Within zone2 and zone3 as noted earlier there will be multiple Focused Transmissions. These focused transmissions may or may not be on a radial arc (e.g. they can be on a horizontal focal line). The separation between them is determined based on the frequency of transmit, the FWHM characteristic of the focused beam at the focal point and focal zone. Since the transmitted energy is to a focal point it stands to reason that beamforming only makes sense within a 'patch' around the focal point since that's the portion of the field of view that was illuminated during insonification. Therefore, within both zone2 and zone3 (zones that utilize focused transmissions), receive beamforming will only be done within 'patches'. These patches will typically be subsections within respective zones. The shapes of the patches may be rectangular (for example if the boundaries between zone1 and zone2 or between zone2 and zone3 are straight-line cuts in the field of view), annular sector (for example if the boundaries between zone1 and zone2 or between zone2 and zone3 are arcs at specific radii delimiting those zones) or other shapes that will typically encompass the focal zone across a vertical span. The typical height of these patches will be the entirety of a zone height (vertical or radial as the case may be). The typical width of these patches will be set based on the FWHM of the transmitted beam at the focal point. An expectation of the patch boundary relative to the focal point of transmission is that the focal point will sit near or close to the center point within each patch.

Figure 4:
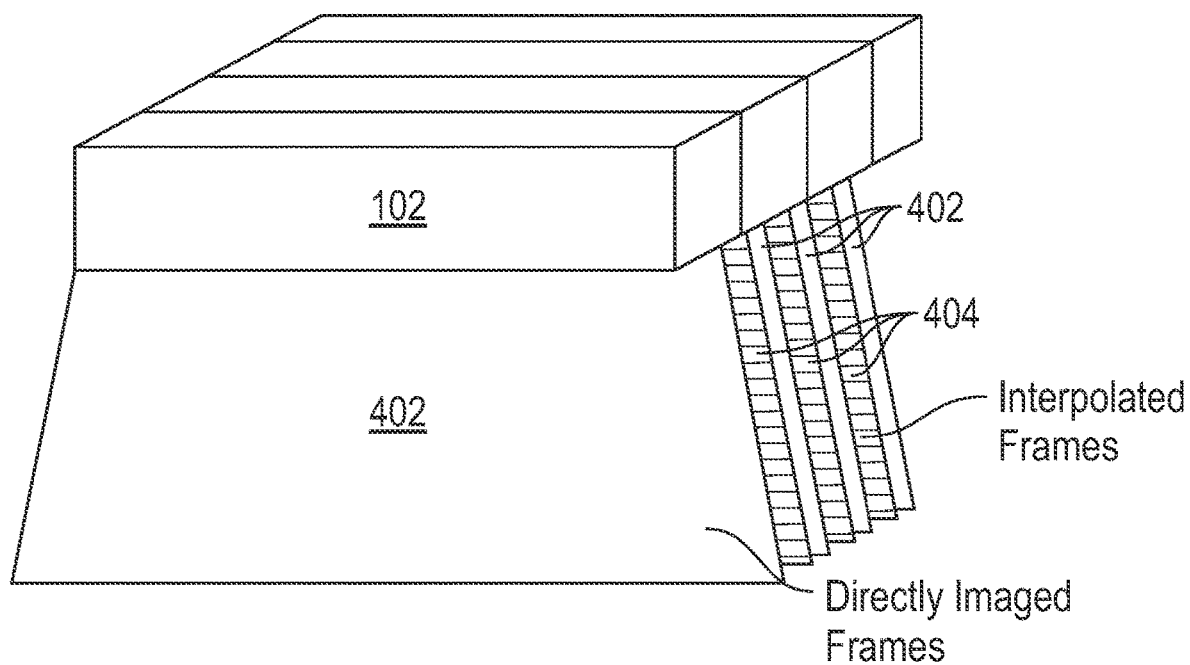
FIG. 4 illustrates an example of interpolating frames that includes pixel-interpolated in-between frames allowing for the 'thick-slice' to have more 2-dimensional frames than just the ones directly underneath each row of elements of the ultrasonic array, where the directly imaged 2D image frames showing the directly imaged frames and the interpolated frames.
Figure 9:
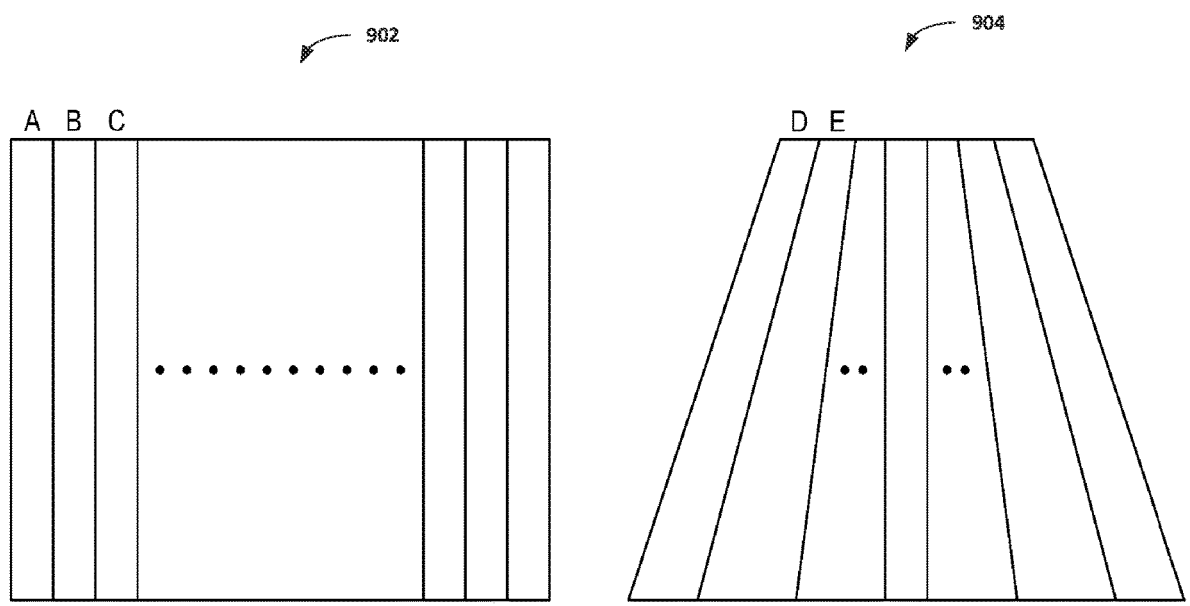
FIG. 9 illustrates an example of an aspect of image compositing, illustrating receive beamforming done within patches where the left portion of this figure shows rectangular-shaped patches and the right portion of this figure are annular sector-shaped.

(ii) Horizontal blending overlap of patches: zone2 and zone3: FIG. 4 illustrates an example of an aspect of image compositing, illustrating receive beamforming done within patches where the left portion of this figure shows rectangular-shaped patches and the right portion of this figure are annular sector-shaped. Both zone2 and zone3 will have adjacent horizontal patches that extend all the way from the left to the right end of a zone as shown in FIG. 9. FIG. 9 illustrates a perpendicular field of view 902 (A B C . . . ) and a wider angle field of view 904 (D E . . . ). The typical effect of beamforming within specific patches with their boundaries as shown in FIG. 9 will be the presence of visible striations that would mark the boundary of each patch being beamformed. To create a smoothly reconstructed image that removes this artifact a careful blending across patches needs to be done. There are multiple ways to do this. Our method of doing this is to have each patch extend out to some extent into each adjacent patch (for example a 50% overlap into adjacent patches allows each pixel within a zone to effectively be covered by computation from two patches: (1) its native patch which has its own focal transmission and (2) it's neighboring patch within which a separate focal transmission event would've been done.

Figure 10:
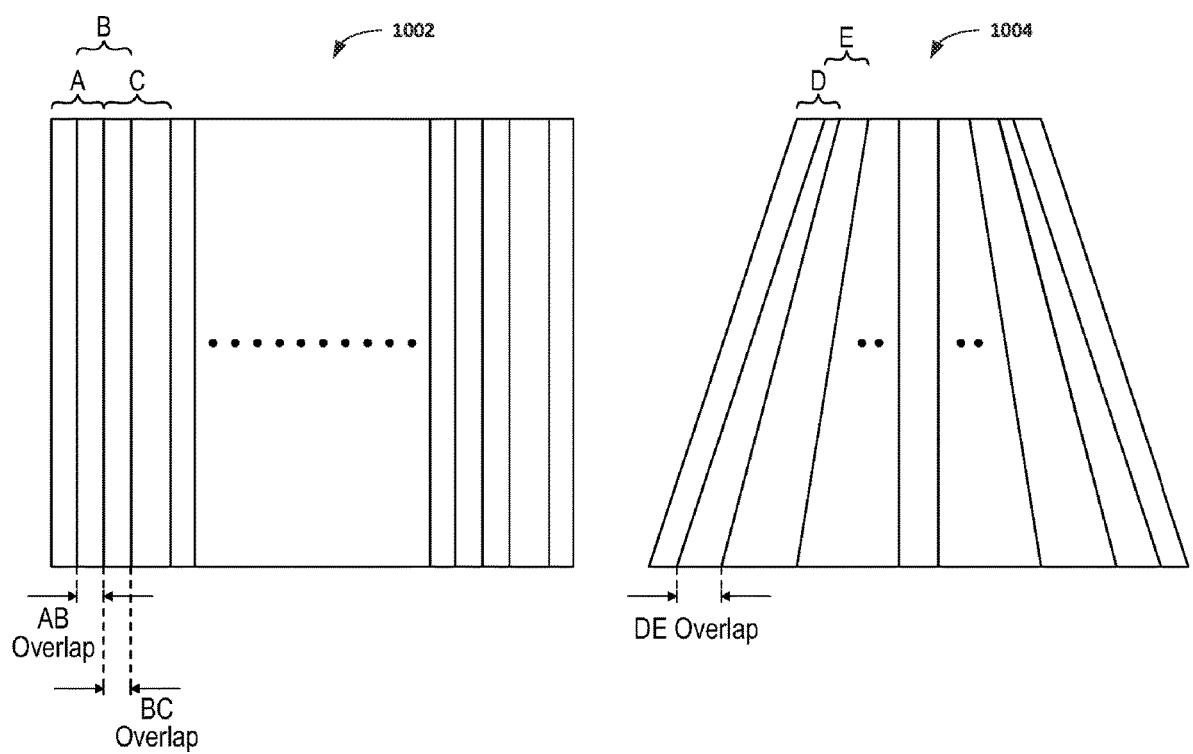
FIG. 10 illustrates an example of how a 50% overlap into adjacent patches may look like for both a perpendicular field of view (see 'AB overlap' region) or for a wider angle field of view (see 'DE' overlap), according to some embodiments.

FIG. 10 illustrates an example of how a 50% overlap into adjacent patches may look like for both a perpendicular field of view 1002 (see 'AB overlap' region) or for a wider angle field of view 1004 (see 'DE' overlap), according to some embodiments. In some embodiments, to be able to do receive beamforming, each patch would be roughly twice as wide (for 50% overlap into adjacent neighbors) as may be indicated by FIG. 9. For the case of radial patches, each patch would have twice as wide an angular span (see 'DE overlap' in FIG. 10) as would otherwise have been indicated in FIG. 9. It's important to note that while the example illustrated in FIG. 10 shows an overlap for each pixel within each patch only from its two neighboring patches and for the shown shapes, there can be other schemes for horizontal blending of patches of many different shapes. For instance, each patch could have a complete overlap (or more) into neighboring patches, which would then lead to each pixel having effectively beamforming information from 3 patches (its own and both of its neighbors). Typically, however, we expect patch overlaps to not be much higher than 50% since the tightness of beam-diameter would lead to there not being enough useful information content from neighbor-of-neighbor focal transmissions. In addition, widening the patch-blending extent too much also runs the danger of picking up energy from side-lobes which can add to noise in the reconstructed image. This sensitivity would be more pronounced at the near-end of the zones closest to the transmitting aperture since neighboring patches would have a higher angular extent. Another method of deciding the amount of patch-overlap has to do with setting a baseline assumption on how many wavelengths of overlap to aim for laterally to pick up enough coherent information for blending (see, for example, "(iii) Horizontal blending techniques for patches" below) to maximize the signal to background noise level during blending.

(iii) Horizontal blending techniques for patches: zone2 and zone3: The easiest method of blending information from neighboring patches of pixels is for each of the pixels, coherently sum up the phase and amplitude information from doing respective receive beamforming for that pixel for its own patch and for any overlapping patch(es) that may also have contained that pixel. Other methods of horizontal blending may consist of a Gaussian blending profile that laterally (along a horizontal cut-line from pixel of interest into neighboring patches) or radially (along a radial cut-line from pixel of interest into neighboring patches) does coherent summation of beamformed values but utilizes a Gaussian weighting algorithm for the accumulated values. Other weighting profiles may also be utilized for relative weighting during this accumulation process. A third method of accumulation may consist of not doing the coherent summation at all and instead utilizing an 'alpha blending' on beamformed and then demodulated pixel brightness values. This alpha-blending would span across neighboring patches similar to how the coherent summation may have been carried out. There may also be hybrid methods that comprise of a mix of coherent summation *and* computed pixel brightness blending across patches. Yet another method of doing horizontal blending is to utilize a contrast-to-noise ratio and/or a signal-to-noise ratio metric that's constantly computed and then used to optimize both the blending curve that'd govern the weighting of pixel brightness values being accumulated (for both coherent summation and/or demodulated pixel brightness accumulation) when moving from the focal point axis for a given focused transmission into the neighboring patches.

(iv) Vertical blending overlap of patches: zone1/zone2 transition and zone2/zone3 transition: The justification for blending of patches vertically at the interfaces between zone1 and zone—or—between zone2 and zone3 follows a similar reasoning as for adjacent horizontal patches within zone2 or zone3. Since the respective zones may utilize different imaging and beamforming techniques (for example, in a manifestation of embodiments of a triple-zone scheme, zone1 will be higher-frequency plane wave imaging whereas zone2 will be tissue harmonic imaging whereas zone3 will be lower frequency imaging for deeper targets), once again the necessity to blend across these zone transitions becomes important. Without an acceptable zone transition blending mechanism, one would otherwise end up with visible demarcation lines between the zones. It is however possible to eliminate them altogether while taking advantage of the sampled signal information across these zones. To create a smoothly reconstructed image that removes this boundary artifact between zones a careful blending across patches needs to be done. There are multiple ways to do this. Our method of doing this is to have each patch extend out to some extent into each vertically adjacent patch (for example a ~10% overlap into vertically adjacent patches allows each overlapped pixel within a zone to effectively be covered by computation from two vertically adjacent patches: (1) its native patch which may have its own focal transmission and (2) its vertically neighboring patch(es) within which a separate focal transmission event may have been done.

Figure 11:
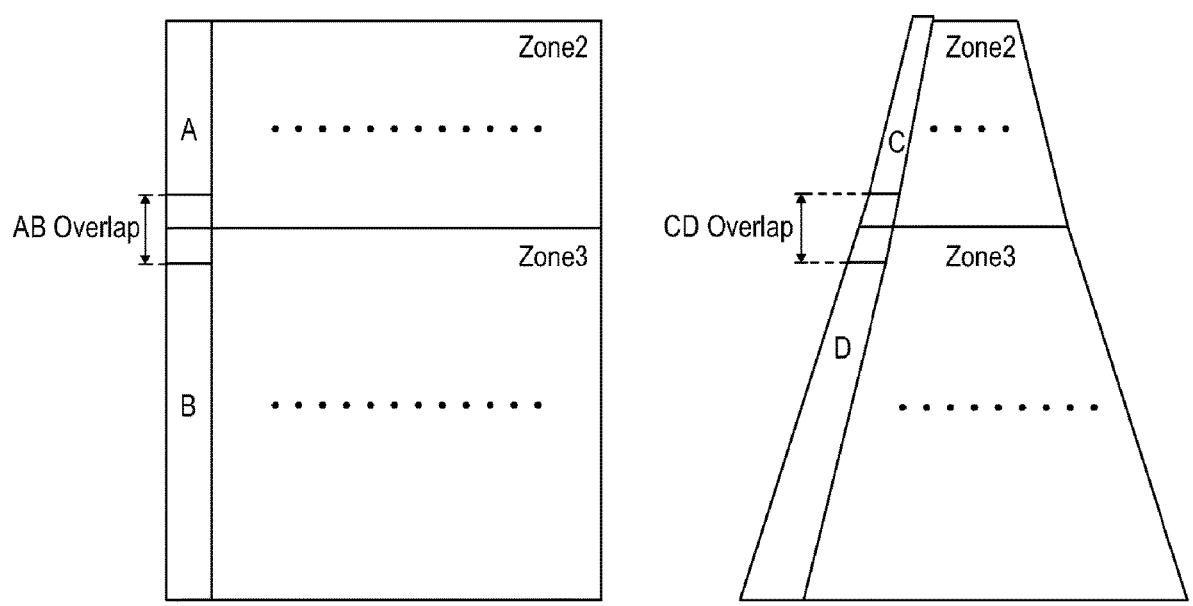
FIG. 11 illustrates in example of how an overlap into vertically adjacent patches may look like both for a perpendicular field of view (see 'AB overlap' region) or for a wider angle field of view (see 'CD' overlap), according to some embodiments.

FIG. 11 illustrates in example of how an overlap into vertically adjacent patches may look like both for a perpendicular field of view (see 'AB overlap' region) or for a wider angle field of view (see 'CD' overlap), according to some embodiments. To be able to do receive beamforming then, each patch would be taller and extend into its neighboring vertical patches. For the case of radial patches, each patch radially extends into the patch(es) above and below it (if applicable) It's important to note that while FIG. 10 shows an overlap for each pixel within each patch only from its neighboring vertical patch and for the shown shapes, there can be other schemes for vertical blending of patches of many different shapes. For instance, each patch could have a diagonal overlap as well into adjacent vertical patches, which could then lead to some pixels for which beamforming would be computed from more than 2 patches (its own and any other patches that overlap it). Typically, however we expect patch overlaps to only be into adjacent vertical neighboring patches since the tightness of beam-diameter would lead to there not being enough useful information content from neighbor-of-neighbor focal transmissions that may necessitate a diagonal neighbor inclusion when doing this vertical blending. In addition, increasing the patch-blending extent too much vertically also runs the danger of losing coherent information directly relevant to the particular patch within a particular zone within which a focused transmission may have been done at a different frequency and/or if it was to be computed utilizing tissue harmonic imaging. This sensitivity would be more pronounced at the far-end of the overlap regions within a zone since that would be deeper within the extent of any zone wherein true beamforming would ideally have already determined the best quality image reconstruction consistent with the method applicable for that zone. Another method of deciding the amount of vertical patch-overlap has to do with setting a baseline assumption on how many wavelengths of overlap to aim for vertically to pick up enough coherent information for blending (see item iii below) to maximize the signal to background noise level during blending.

(v) Vertical blending techniques for patches: zone1/zone2 transition and zone2/zone3 transition: The easiest method of blending information from vertical neighboring patches for each pixel is to coherently sum up the phase and amplitude information from doing respective receive beamforming for that pixel for its own patch and for any overlapping patch(es) that may also have contained that pixel. Other methods of vertical blending may consist of a Gaussian blending profile that vertically (along a vertical cut-line from pixel of interest into neighboring vertical patches) or radially (along a radial cut-line from pixel of interest into neighboring vertical patches) does coherent summation of beamformed values but utilizes a Gaussian weighting algorithm for the accumulated values. Other weighting profiles may also be utilized for relative weighting during this accumulation process. A third method of accumulation may consist of not doing the coherent summation at all and instead utilizing an 'alpha blending' on beamformed and then demodulated pixel brightness values. This alpha-blending would span across neighboring vertical patches similar to how the coherent summation may have been carried out. There may also be hybrid methods that comprise of a mix of coherent summation *and* computed pixel brightness blending across patches. Yet another method of doing vertical blending is to utilize a contrast-to-noise ratio and/or a signal-to-noise ratio metric that's constantly computed and then used to optimize both the blending curve that'd govern the weighting of pixel brightness values being accumulated (for both coherent summation and/or demodulated pixel brightness accumulation) when moving vertically or radially along within the overlap region across neighboring vertical patches d. Other Considerations:

(i) Ultrasonic Array Frequency bandwidth: It's important to note that according to some embodiments the ultrasonic array that can be utilized to enable the triple-zone, multi-frequency imaging scheme would have: (a) a wide enough bandwidth that it will support Tissue Harmonic Imaging, and (b) enough output ultrasonic pressure to be able to penetrate deep enough to make all zones viable. In case neither (a) nor (b) is true, each zone however can still be imaged at its own frequency. In general, the imaging frequency would decrease as one goes from zone1 to zone2 to zone3 to construct the deepest image possible since the amount of attenuation is directly proportional (in dB scale) to frequency.

(ii) Electrical systems and transmit voltages: Similar to the frequency of transmission, it may also be necessary to adjust the voltage at which the system drives elements in the ultrasonic array. Emitted energy is typically proportional to the square of voltage. In general, one would increase the voltage for deeper imaging (roughly coinciding with zone3 being at a higher voltage than zone2 which would be at a higher voltage than zone 1). However, there are multiple dimensions to this which include but are not limited to the frequency of transmission, the transmit aperture and transmit apodization, sharpness of focus obtainable from the ultrasonic array and its lens focal depth setting, the granularity at which elements may be sequenced in time to obtain an expected wavefront shape etc. Because of the above noted factors, the Transmit voltage will just become one aspect of a multidimensional optimization. It can however be set either by a priori knowledge or expectation of what combination may work best, or empirically via experimentation with the entire integrated system, or as an adaptive system that looks for the best obtainable contrast-to-noise ratio (CNR) or signal-to-noise ratio (SNR) or other metrics (e.g. clearing around known target cysts within a phantom as part of a calibration step, quality of background speckle, minimum acceptable illumination and range of generated pixel brightness values etc.).

(iii) Beam diameter, Pulse Repetition Frequency, Attenuation and a few other factors: A few aspects that can have direct impact on the extent of each zone, width of each patch, etc., are noted here. These are a few non-limiting examples of items for consideration to be adjusted for the entire imaging scheme to jointly produce a good quality image. As a one of ordinary skill in the art will appreciate, additional aspects can also be considered, or fewer aspects, depending at least in part the implementation and particular goals of the implementation. Such items may include:

1. Attenuation: The relative thicknesses and location of muscle vs tissue which typically have a 2× attenuation ratio vs each other will influence the relative thickness of various zones. While the possibility of using an AI system to automatically determine which medium is of what type is certainly there, by and large this is an operator-setting and will be set a priori at the beginning of an exam by operator (e.g. by picking a clinical modality such as 'small parts' or 'abdominal' or 'lung' etc.) and the information then used by the ultrasound system to set reasonable default depths and boundaries for each of the three zones.

2. Lens focal depth: The focal depth of the lens that would house the ultrasonic array would likewise be set to maximize the final reconstructed image quality. In general, since zone1 is a Plane Wave imaging zone it prefers 'unfocused transmissions', which zone2 and zone3 are to be done with 'focused transmission'. Therefore, a lens focal length which typically sits at the boundary between zone2 and zone3 will be preferable since it'll (likely) be far enough away from zone1 to allow zone1 to be treated as an 'unfocused transmit' region, while allowing lens focusing to improve the elevational resolution of the transmitted beam for each of the focused transmissions into zone2 and zone3.

3. Array dimensions: The specific azimuth and elevational pitches and transmit frequencies chosen for the array have direct impact on the beam diameter and hence will directly impact the FWHM (full width at half maximum) in each focused patch within each zone (zone2 and zone3 in this disclosure). In additional the specific frequency of transmission will have its own bandwidth roll-off for a particular array. Therefore, it's important to have the array dimensions and all transmit frequencies for it (not just the center frequency) to together enable the overall imaging scheme described in this disclosure. In addition, the ability to image a wide FOV (field of view) relies on the ability to electronically steer the focal point of the emitted transmit wave to various points which may or may not be directly underneath the array. That requires an azimuth separation of less than a wavelength of the transmitted wave frequency.

4. Focal gain of array: The ability to electronically steer a beam at a given frequency to an effective focal point that minimizes its FWHM (or at least sets it at the desired extent) is also an important determinant that'll set the number of focused transmission patches. This FWHM is a key indicator of how easily an ultrasound system can discern objects within or out of its focused beam. In addition, a high focal gain will lead to a relatively high illumination and hence less need to repeatedly insonify the same or neighboring regions to extract a higher SNR (signal to noise ratio).

5. Beam diameter: The diameter of a focused beam is a function of many different factors including the targeted transmit beam shape, the granularity of sequenced transmission pulses across elements within a row or across multiple rows (if a 2-dimensional array were to be used for transmission), the frequency of transmission, the ultrasonic array dimensions themselves (e.g. azimuth and elevational separation) and the medium itself (with its refraction characteristics for example) etc. This beam-diameter is a first-order determinant of the width of patches. A focused beam with a tight beam diameter will in general produce better images within its patch. A sequence of patches that are adequate to that beam diameter will then cover the entire imaged area within a zone.

6. PRF (Pulse repetition frequency): PRF refers to the rate at which transmissions may be emitted by the ultrasonic array. It has a direct dependence on the depth being imaged *and* the imaging scheme being utilized. There are many schemes for PRF, from pulses emitted at regular intervals to 'burst mode' where as many pulses as can be rapidly sent out and acquired are sent and then a high quality image composited, and then the entire system may go into a somewhat lower power state before the next 'burst' may happen. As applied to zone2 and zone3, the PRF needs to be set such that each patch within each of these zones can successively get a focused beam and then its echoes completely acquired before the next pulse is initiated. In the context of zone1, the PRF refers to the rate at which multiple unfocused plane waves may be emitted to acquire a high quality image within this zone.

Figure 12:
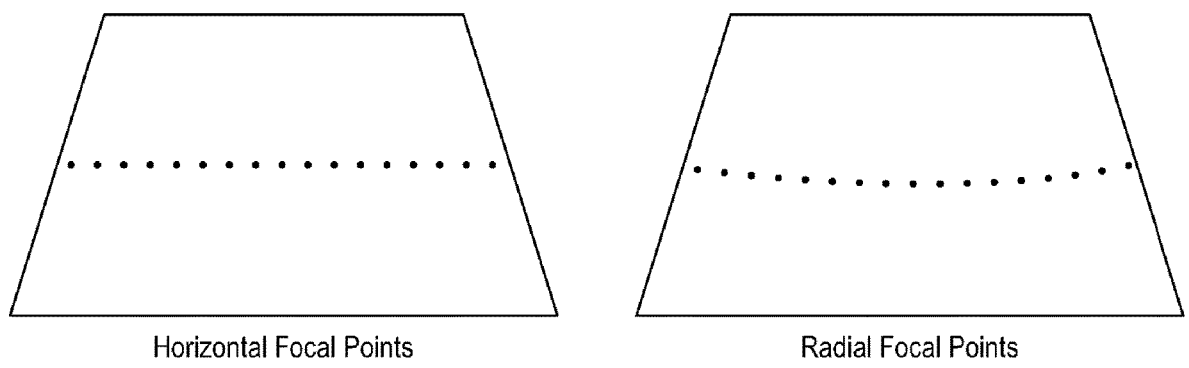
FIG. 12 illustrates an example of how the focal points for patches within zone2 or zone3 could be arranged in either a Horizontal or Radial scheme, with the left portion of this figure showing horizontal focal points and the right portion of this figure showing radial focal points, according to some embodiments.

(iv) Focal point arrangements within zone2 and zone3: It's important to note that the focal points within zone2 or zone3 may be arranged to fall on a Horizontal line within this zone, or a Radial line within this zone. There are other arrangements possible too which may explicitly account for relatively reduced focal gain along the edges of a zone (especially in the part of the zone nearer to the array) and use that to pull in the focal points into a light parabolic shape. FIG. 12 illustrates an example of how the focal points for patches within zone2 or zone3 could be arranged in either a Horizontal or Radial scheme, with the left portion of this figure showing horizontal focal points and the right portion of this figure showing radial focal points, according to some embodiments. It is also possible to place multiple focal points within the same patch via separate focused transmissions (as separate transmit events into the same patch and then time-averaged or accumulated over these sequential transmissions for receive beamforming purposes). In this case each patch may be treated as a 'super-patch' encompassing multiple transmissions. However, in this invention, each focused transmission to any particular point within the medium is considered to have its own patch. A focused transmission, however, has overlaps into horizontal or vertical neighboring patches and/or regions for receive beamforming purposes as described above in section c Image Compositing.

Figure 13:
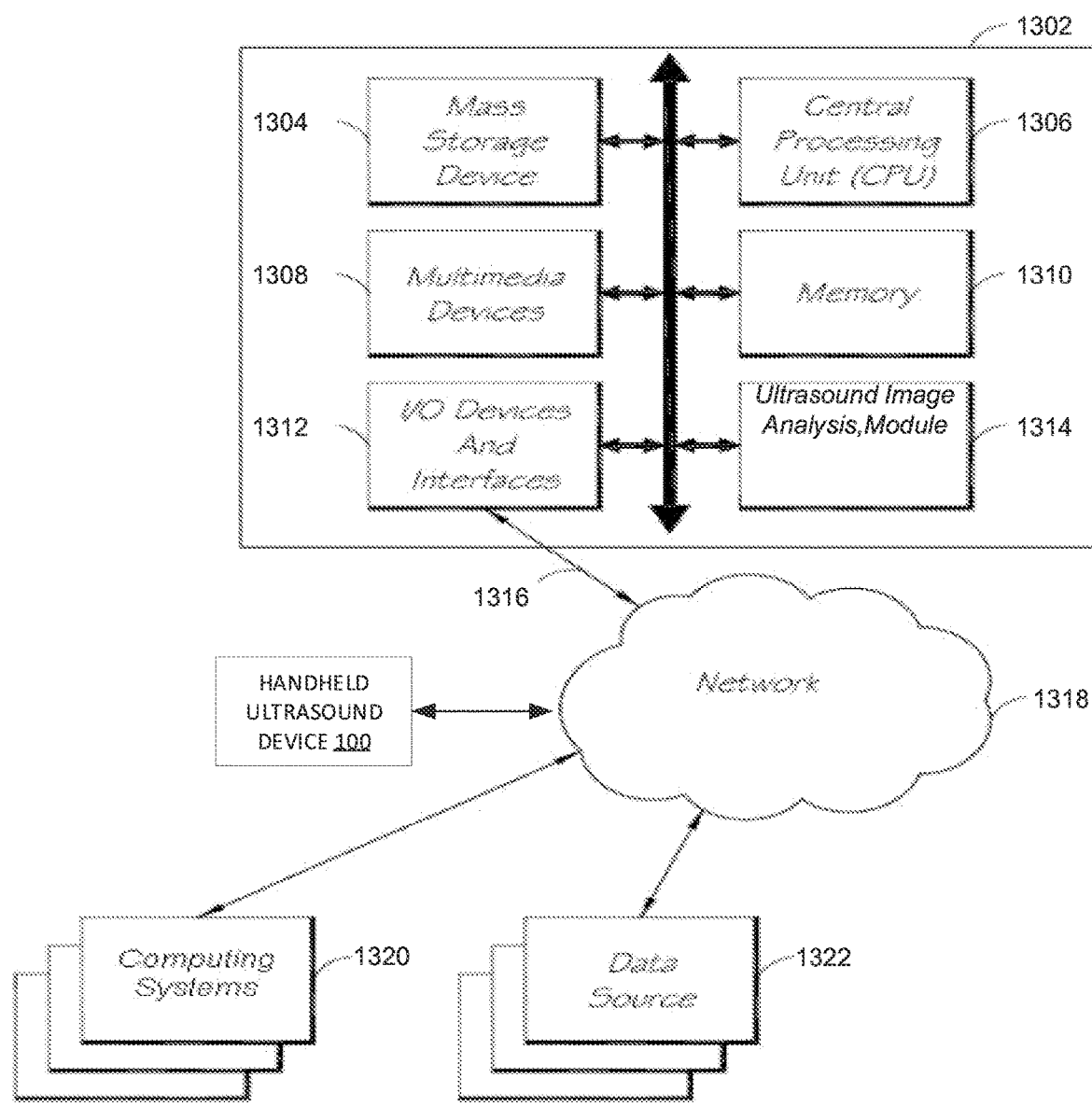
FIG. 13 illustrates a system that includes a handheld ultrasonic device in communication with one or more other devices network, the network being either wired or wireless.

FIG. 13 illustrates a system that includes a handheld ultrasonic device in communication with one or more other devices network, the network being either wired or wireless. In some embodiments, the systems, processes, and methods described herein are implemented using a computing system, such as the one illustrated in FIG. 13. Although this disclosure indicates that the disclosed methods, processes, and systems can be implemented in a handheld ultrasonic device, such methods, processes, and systems can also be implemented in a non-handheld ultrasonic device (e.g., any ultrasonic device). The example computer system 1302 is in communication with one or more computing systems 1320 and/or one or more data sources 1322 via one or more networks 1318. In various embodiments, the handheld ultrasound system 100 can also include functionality and components described in reference to the computer system 1302. For example, in some embodiments, all of the image formation processing is performed on the handheld ultrasound device 100, and images generated by the device 100 are provided via a network 1318 (wireless or wired) to one or more other computer systems or devices for storage, further processing or communication to another device, or for display. In some embodiments, the handheld ultrasound device 100 provides generated information to a mobile device, headset, smart phone, etc. While FIG. 13 illustrates an embodiment of a computing system 1302, it is recognized that the functionality provided for in the components and modules of computer system 1302 may be combined into fewer components and modules, or further separated into additional components and modules.

The computer system 1302 can comprise an ultrasound image analysis module 1314 that carries out functions, methods, acts, and/or processes for analysis and/or further processing of ultrasound information generated by an ultrasound device, for example, a handheld ultrasound device 100 described herein. The ultrasound image analysis module 1314 can be executed on the computer system 1302 by a central processing unit 1306 discussed further below.

In general the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1302 includes one or more processing units (CPU) 1306, which may comprise a microprocessor. The computer system 1302 further includes a physical memory 1310, such as random access memory (RAM) for temporary storage of information, a read only memory (ROM) for permanent storage of information, and a mass storage device 1304, such as a backing store, hard drive, rotating magnetic disks, solid state disks (SSD), flash memory, phase-change memory (PCM), 3D)(Point memory, diskette, or optical media storage device. Alternatively, the mass storage device may be implemented in an array of servers. Typically, the components of the computer system 1302 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1302 includes one or more input/output (I/O) devices and interfaces 1312, such as a keyboard, mouse, touch pad, and printer. The I/O devices and interfaces 1312 can include one or more display devices, such as a monitor, that allows the visual presentation of data to a user. More particularly, a display device provides for the presentation of GUIs as application software data, and multi-media presentations, for example. The I/O devices and interfaces 1312 can also provide a communications interface to various external devices. The computer system 1302 may comprise one or more multi-media devices 1308, such as speakers, video cards, graphics accelerators, and microphones, for example.

The computer system 1302 may run on a variety of computing devices, such as a server, a Windows server, a Structure Query Language server, a Unix Server, a personal computer, a laptop computer, and so forth. In other embodiments, the computer system 1302 may run on a cluster computer system, a mainframe computer system and/or other computing system suitable for controlling and/or communicating with large databases, performing high volume transaction processing, and generating reports from large databases. The computing system 1302 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1302 illustrated in FIG. 13 is coupled to a network 1318, such as a LAN, WAN, or the Internet via a communication link 1316 (wired, wireless, or a combination thereof). Network 1318 communicates with various computing devices and/or other electronic devices. Network 1318 is communicating with one or more computing systems 1320 and one or more data sources 1322. The Ultrasound Image Analysis Module 1314 may access or may be accessed by computing systems 1320 and/or data sources 1322 through a web-enabled user access point. Connections may be a direct physical connection, a virtual connection, and other connection type. The web-enabled user access point may comprise a browser module that uses text, graphics, audio, video, and other media to present data and to allow interaction with data via the network 1318.

Access to the Ultrasound Image Analysis Module 1314 of the computer system 1302 by computing systems 1320 and/or by data sources 1322 may be through a web-enabled user access point such as the computing systems' 1320 or data source's 1322 personal computer, cellular phone, smartphone, laptop, tablet computer, e-reader device, audio player, or other device capable of connecting to the network 1318. Such a device may have a browser module that is implemented as a module that uses text, graphics, audio, video, and other media to present data and to allow interaction with data via the network 1318.

The output module may be implemented as a combination of an all-points addressable display such as a cathode ray tube (CRT), a liquid crystal display (LCD), a plasma display, or other types and/or combinations of displays. The output module may be implemented to communicate with input devices 1312 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1302 may comprise a physical or logical connection established between a remote microprocessor and a mainframe host computer for the express purpose of uploading, downloading, or viewing interactive data and databases on-line in real time. The remote microprocessor may be operated by an entity operating the computer system 1302, including the client server systems or the main server system, and/or may be operated by one or more of the data sources 1322 and/or one or more of the computing systems 1320. In some embodiments, terminal emulation software may be used on the microprocessor for participating in the micro-mainframe link.

In some embodiments, computing systems 1320 who are internal to an entity operating the computer system 1302 may access the Ultrasound Image Analysis Module 1314 internally as an application or process run by the CPU 1306.

The computing system 1302 may include one or more internal and/or external data sources (for example, data sources 1322). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1302 may also access one or more databases 1322. The databases 1322 may be stored in a database or data repository. The computer system 1302 may access the one or more databases 1322 through a network 1318 or may directly access the database or data repository through I/O devices and interfaces 1312. The data repository storing the one or more databases 1322 may reside within the computer system 1302.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a web site and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Figure 14:
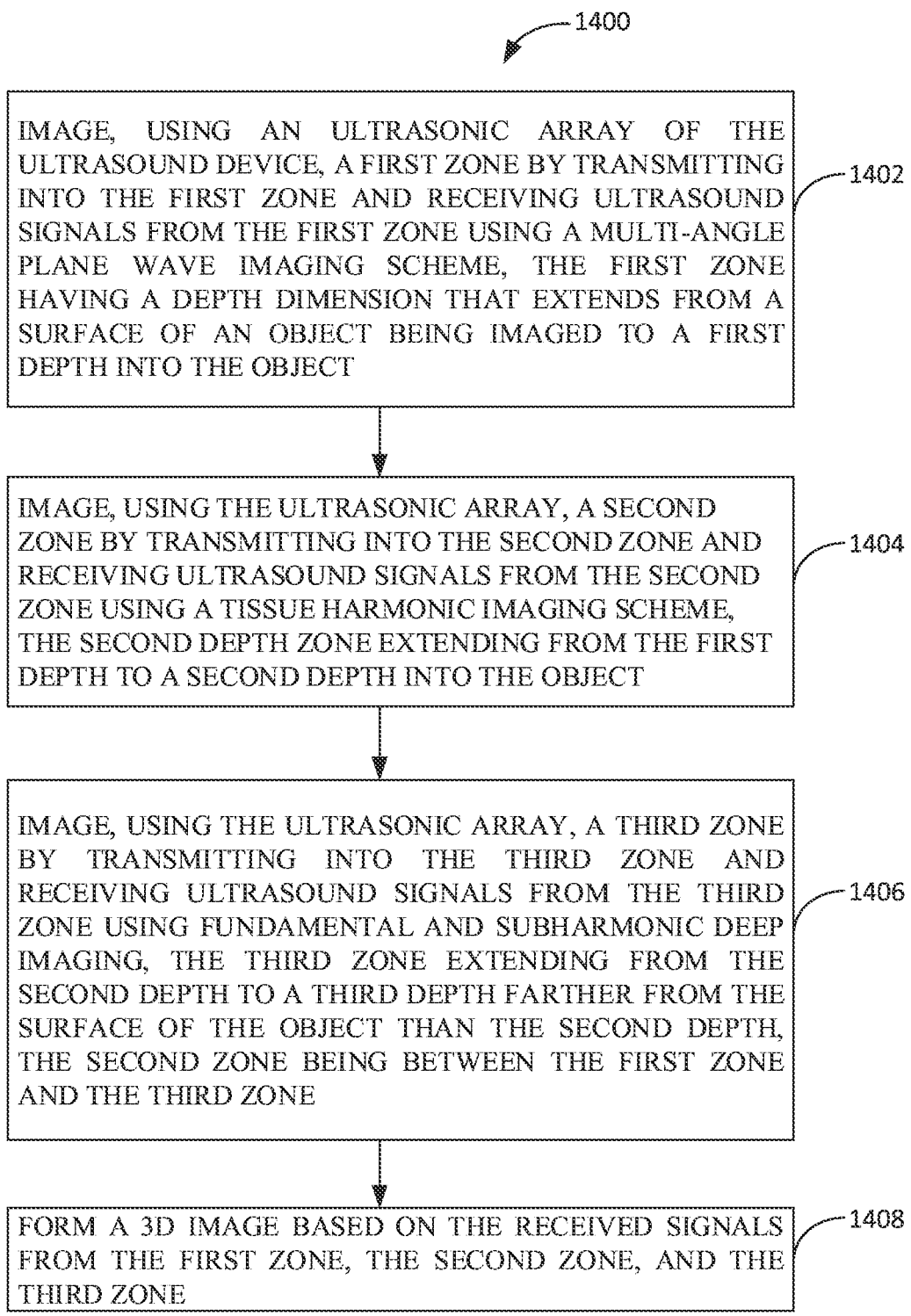
FIG. 14 illustrates a flowchart of a process for three zone ultrasonic imaging where (i) imaging the first zone or the second zone includes forming a thick slice image of the first zone or the second zone, or (ii) imaging the first zone and the second zone includes forming a thick slice image of the first zone and the second zone.

FIG. 14 illustrates a flowchart of a process 1400 for three zone ultrasonic imaging where (i) imaging the first zone or the second zone includes forming a thick slice image of the first zone or the second zone, or (ii) imaging the first zone and the second zone includes forming a thick slice image of the first zone and the second zone. At block 1402 the process 1400 of generating a 3-dimensional image of a target area that includes multiple depth zones for acquiring data using a handheld ultrasound device images using an ultrasonic array of the ultrasound device, a first zone by transmitting into the first zone and receiving ultrasound signals from the first zone using a multi-angle plane wave imaging scheme. The first zone has a depth dimension that extends from a surface of an object being imaged to a first depth into the object.

At block 1404 the process 1400 images, using the ultrasonic array, a second zone by transmitting into the second zone and receiving ultrasound signals from the second zone using a tissue harmonic imaging scheme, the second depth zone extending from the first depth to a second depth into the object, the second depth being farther from the surface of the object than the first depth, the first zone being between the second zone and the ultrasonic array. In some embodiments, imaging the first zone or the second zone includes forming a thick slice image of the first zone or the second zone; or in some embodiments, imaging the first zone and the second zone includes forming a thick slice image of the first zone and the second zone.

At block 1406 the process 1400 images, using the ultrasonic array, a third zone by transmitting into the third zone and receiving ultrasound signals from the third zone using fundamental and subharmonic deep imaging. The third zone extends from the second depth to a third depth farther from the surface of the object than the second depth, the second zone being between the first zone and the third zone.

At block 1408 the process 1400 forms a 3D image based on the received signals from the first zone, the second zone, and the third zone. In some embodiments, the process 1400 further comprises horizontally blending patches in the second zone and the third zone. each patch in the second zone and each patch in the third zone has a height of the entirety of the respective zone. In some embodiments of process 1400, horizontally blending patches includes coherently summing respective phase and the amplitude information from neighboring patches for each pixel from respective receive beamforming for a pixel of its own patch and for any overlapping patches that may also contain said pixel. In some embodiments of process 1400, the process further comprises vertically blending patches (or portions of the received ultrasound signals) at interfaces between the first zone and the second zone, and the second zone and the third zone. For example, interpolating between the information from the first zone and the second zone, and/or the second zone and the third zone.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

To provide for interaction with a user, one or more aspects or features of the subject matter described herein may be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices may be used to provide for interaction with a user as well. For example, feedback provided to the user may be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

Example Embodiments

The following are examples of certain embodiments of the invention. However, these listed examples of embodiments are not meant to limit the invention in any way, and other embodiments are also possible.

An Embodiment A can include a method of generating a 3-dimensional (3D) image of a target area of an object that includes multiple depth zones for acquiring data using a handheld ultrasound device. The method can include imaging, using an ultrasonic array of the ultrasound device, a first zone by transmitting and receiving ultrasound signals using a multi-angle plane wave imaging scheme, the first zone having a depth dimension that extends from a surface of an object being imaged to a $1^{st}$ depth into the object. The object can be, for example, a portion of a human or an animal, or any other object that has a volume that can be imaged with ultrasound. The method can include imaging, using the ultrasonic array, a second zone by transmitting and receiving ultrasound signals using a tissue harmonic imaging scheme, the second depth zone extending from the 1st depth to a 2nd depth into the object, the $2^{nd}$ depth being farther from the surface of the object than the $1^{st}$ depth, the first zone being between the second zone and the ultrasonic array, wherein imaging the first zone or the second zone includes forming a thick slice image of the first zone or the second zone, or imaging the first zone and the second zone includes forming a thick slice image of the first zone and the second zone. The method can further include imaging, using the ultrasonic array, a third zone by transmitting and receiving ultrasound signals in the third zone using fundamental and subharmonic deep imaging, the third zone extending from the $2^{nd}$ depth to a $3^{rd}$ depth farther from the surface of the object than the $2^{nd}$ depth, the second zone being between the first zone and the third zone, and forming a 3D image based on the received signals from the first zone, the second zone, and the third zone.

Embodiment B can include Embodiment A, wherein the $1^{st}$ depth is in the range of 0.5 cm to about 10 cm.

Embodiment C can include Embodiment A, wherein the $2^{nd}$ depth is in the range of 2 cm to about 18 cm.

Embodiment D can include Embodiment A, wherein the $3^{rd}$ depth is in the range of 6 cm to about 18 cm.

Embodiment E can include Embodiment A, wherein the 1st depth is about 3.2 cm.

Embodiment F can include Embodiments A or E, wherein the $2^{nd}$ depth is about 9.6 cm.

Embodiment G can include any one of Embodiments A-F, wherein the $3^{rd}$ depth is about 19.2 cm.

Embodiment H can include Embodiments A, wherein a depth extent of the imaging of the first zone corresponds to a F# of 0 to about 1.

Embodiment I can include Embodiments A or H, wherein a depth extent of the imaging of the second zone corresponds to an F# of about 1 to about 3.

Embodiment J can include Embodiments A, H or I, wherein a depth extent of the imaging of the third zone corresponds to an F# of about 3 to about 6.

Embodiment K can include Embodiment A, wherein imaging the first zone comprises accumulating signals from a plurality of angles of plane wave transmissions to coherently accumulate beamformed images and form a composite image.

Embodiment L can include Embodiment K, wherein accumulating signals for a plurality of angles of plane waves transmissions comprises accumulating signals for 5 or more angles.

Embodiment M can include Embodiment K, wherein accumulating signals for a plurality of angles of plane waves transmissions comprises accumulating signals for 9 or more angles.

Embodiment N can include Embodiment K, wherein accumulating signals for a plurality of angles of plane waves transmissions comprises accumulating signals for 11 or more angles.

Embodiment O can include Embodiment A, further comprising processing the signals received in the second zone using power pulse inversion processing.

Embodiment P can include Embodiment A, wherein imaging the second zone comprise transmitting a plurality of focused ultrasound transmissions at a frequency f.

Embodiment Q can include Embodiment A, wherein imaging the third zone comprises utilizing focused transmits wherein transmitting and receiving the ultrasound signals are at the same frequency.

Embodiment R can include Embodiment A, further comprising horizontally blending patches in the second zone and the third zone.

Embodiment S can include Embodiment R, wherein each patch in the second zone and each patch in the third zone has a height of the entirety of the respective zone.

Embodiment T can include Embodiment R, wherein horizontally blending patches comprises coherently summing respective phase and the amplitude information from neighboring patches for each pixel from respective receive beamforming for a pixel of its own patch and for any overlapping patches that may also contain said pixel.

Embodiment U can include Embodiment A, further comprising vertically blending patches at interfaces between the first zone and the second zone, and the second zone and the third zone.

Embodiment V can include Embodiment A, wherein the array comprises 4 rows, each row having 128 elements.

Embodiment W can include Embodiment V, further comprising addressing each element of the array during imaging of the first zone, imaging the second zone, and imaging the third zone.

Embodiment X can include Embodiment A, wherein imaging the first zone includes employing a multiplexing scheme to simultaneously transmit ultrasonic signals from ultrasonic elements of the ultrasonic array that are positioned in the ultrasonic array in a same elevation direction.

Embodiment Y can include Embodiment A, wherein imaging the first zone includes employing a multiplexing scheme to simultaneously transmit ultrasonic signals from ultrasonic elements of the ultrasonic array that are positioned in different rows of the ultrasonic array.

Embodiment Z can include Embodiment A, wherein imaging the first zone includes employing a multiplexing scheme to transmit ultrasonic signals from each of a plurality of groups of ultrasonic elements of the ultrasonic array, each group of ultrasonic elements in a separate row of the ultrasonic array and positioned in a same elevation direction in the ultrasonic array, the multiplexing scheme driving each of the ultrasonic elements in a group to simultaneously transmit ultrasonic signals.

Embodiment AA can include a handheld ultrasound device, comprising a plurality of rows of ultrasonic elements, the rows arranged in parallel to form an array, the ultrasonic elements of the array characterized by an elevation pitch between ultrasonic elements in adjacent rows and an azimuth pitch between ultrasonic elements within the same row; a plurality of N-way multiplexers, each N-way multiplexor coupled to at least one element in each row; and a plurality of high-voltage pulsers configured to provide high voltage pulses to the ultrasonic elements the plurality of multiplexers; a plurality of analog front-end receivers coupled to the N-way multiplexers and configured to amplify and digitize received ultrasonic signals; and a control system coupled to the plurality of N-way multiplexers, the plurality of high-voltage pulsers, and the plurality of analog front-end receivers. The controls system are operable for imaging, using the array, a first zone by transmitting and receiving ultrasound signals using a multi-angle plane wave imaging scheme, the first zone having a depth dimension that extends from a surface of an object being imaged to a $1^{st}$ depth into the object; imaging, using the array, a second zone by transmitting and receiving ultrasound signals using a tissue harmonic imaging scheme, the second depth zone extending from the 1st depth to a $2^{nd}$ depth into the object, the $2^{nd}$ depth being farther from the surface of the object than the depth, the first zone being between the second zone and the ultrasonic array, wherein imaging the first zone or the second zone includes forming a thick slice image of the first zone or the second zone, or imaging the first zone and the second zone includes forming a thick slice image of the first zone and the second zone; imaging, using the ultrasonic array, a third zone by transmitting and receiving ultrasound signals in the third zone using fundamental and subharmonic deep imaging, the third zone extending from the $2^{nd}$ depth to a $3^{rd}$ depth farther from the surface of the object than the 2nd depth, the second zone being between the first zone and the third zone; and forming an image based on the received signals from the first zone, the second zone, and the third zone.

Implementation Consideration

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

To provide for interaction with a user, one or more aspects or features of the subject matter described herein may be implemented on a computer having a display device for displaying information to the user, and an input interface by which the user may provide input to the computer. Other kinds of devices may be used to provide for interaction with a user as well. Other possible input devices include touch screens or other touch-sensitive devices such as single or multi-point resistive or capacitive trackpads, voice recognition hardware and software, and the like.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays, or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to methods, apparatus (systems), and computer program products according to embodiments of the disclosure. It will be understood that each method can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The technology described herein illustrates certain architecture, functionality, and operation of possible implementations of systems, methods, and computer program products according to various embodiments of the present disclosure. In this regard, the functionality can be implemented in software or hardware. The functionality can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like.

It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, may represent endpoints or starting points, and ranges for any combination of the data points. For example, if a particular data point "10" and a particular data point "15" may be disclosed, it is understood that greater than, greater than or equal to, less than, less than or equal to, and equal to 10 and 15 may be considered disclosed as well as between 10 and 15. It is also understood that each unit between two particular units may be also disclosed. For example, if 10 and 15 may be disclosed, then 11, 12, 13, and 14 may be also disclosed.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A method of generating a 3-dimensional (3D) image of a target area that includes multiple depth zones for acquiring data using a handheld ultrasound device, the method comprising:
   imaging, using an ultrasonic array of the ultrasound device, a first zone by transmitting into the first zone and receiving ultrasound signals from the first zone using a multi-angle plane wave imaging scheme, the first zone having a depth dimension that extends from a surface of an object being imaged to a first depth into the object;

imaging, using the ultrasonic array, a second zone by transmitting into the second zone and receiving ultrasound signals from the second zone using a tissue harmonic imaging scheme, the second depth zone extending from the first depth to a second depth into the object, the second depth being farther from the surface of the object than the first depth, the first zone being between the second zone and the ultrasonic array, wherein imaging at least one of the first zone or the second zone includes forming a thick slice image of at least one of the first zone or the second zone;

imaging, using the ultrasonic array, a third zone by transmitting into the third zone and receiving ultrasound signals from the third zone using fundamental and subharmonic deep imaging, the third zone extending from the second depth to a third depth farther from the surface of the object than the second depth, the second zone being between the first zone and the third zone;

forming a 3D image based on the received signals from the first zone, the second zone, and the third zone;

extending at least one first patch from the second zone such that the at least one first patch overlaps with at least one first horizontally adjacent patch to form a first overlapping area;

extending at least one second patch from the third zone such that the at least one second patch overlaps with at least one second horizontally adjacent patch to form a second overlapping area;

blending the at least one first patch with the at least one first horizontally adjacent patch in the first overlapping area;

blending the at least one second patch with the at least one second horizontally adjacent patch in the second overlapping area;

extending at least one third patch from the second zone such that the at least one third patch overlaps with at least one vertically adjacent patch in the third zone to form a third overlapping area; and blending the at least one third patch with the at least one vertically adjacent patch in the third overlapping area.

2. The method of claim 1, wherein the first depth is in the range of 0.0 cm to about 10 cm, wherein the second depth is in the range of 2 cm to about 18 cm, and wherein the third depth is in the range of 6 cm to about 18 cm.

3. The method of claim 1, wherein a depth extent of the imaging of the first zone corresponds to an F# of 0 to about 1, wherein the F# refers to a ratio of a focal length to a diameter of an entrance pupil of the ultrasound device.

4. The method of claim 1, wherein a depth extent of the imaging of the second zone corresponds to an F# of about 1 to about 3, wherein the F# refers to a ratio of a focal length to a diameter of an entrance pupil of the ultrasound device.

5. The method of claim 1, wherein a depth extent of the imaging of the third zone corresponds to an F# of about 3 to about 6, wherein the F# refers to a ratio of a focal length to a diameter of an entrance pupil of the ultrasound device.

6. The method of claim 1, wherein imaging the first zone further comprises accumulating signals from a plurality of angles of plane wave transmissions to coherently accumulate beamformed images, and forming a composite image from the accumulated signals.

7. The method of claim 6, wherein accumulating signals for a plurality of angles of plane waves transmissions comprises accumulating signals for five or more different angles.

8. The method of claim 6, wherein accumulating signals for a plurality of angles of plane waves transmissions comprises accumulating signals for nine or more different angles.

9. The method of claim 6, wherein accumulating signals for a plurality of angles of plane waves transmissions comprises accumulating signals for 11 or more angles.

10. The method of claim 1, wherein imaging the third zone comprises utilizing focused transmits of ultrasounds signals, wherein the transmitted and received ultrasound signals are at the same frequency.

11. The method of claim 1, wherein each patch in the second zone and each patch in the third zone has a height of the entirety of the respective zone.

12. The method of claim 1, wherein horizontally blending patches comprises coherently summing respective phase and the amplitude information from neighboring patches for each pixel from respective receive beamforming for a pixel of its own patch and for any overlapping patches that may also contain said pixel of its own patch.

13. The method of claim 1, further comprising vertically blending patches at interfaces between the first zone and the second zone, and the second zone and the third zone.

14. The method of claim 1, wherein the array comprises 4 rows, each row having 128 elements, and the method further comprises addressing each element of the array during imaging of the first zone, imaging the second zone, and imaging the third zone.

15. The method of claim 1, wherein imaging the first zone includes employing a multiplexing scheme to simultaneously transmit ultrasonic signals from ultrasonic elements of the ultrasonic array that are positioned in the ultrasonic array in a same elevation direction.

16. The method of claim 1, wherein imaging the first zone includes employing a multiplexing scheme to simultaneously transmit ultrasonic signals from ultrasonic elements of the ultrasonic array that are positioned in different rows of the ultrasonic array.

17. The method of claim 1, wherein imaging the first zone includes employing a multiplexing scheme to transmit ultrasonic signals from each of a plurality of groups of ultrasonic elements of the ultrasonic array, each group of ultrasonic elements in a separate row of the ultrasonic array and positioned in a same elevation direction in the ultrasonic array, the multiplexing scheme driving each of the ultrasonic elements in a group to simultaneously transmit ultrasonic signals.

18. A handheld ultrasound device, comprising:
a plurality of rows of ultrasonic elements, the rows arranged in parallel to form an array, the ultrasonic elements of the array characterized by an elevation pitch between ultrasonic elements in adjacent rows and an azimuth pitch between ultrasonic elements within the same row;
a plurality of multiplexers, each multiplexor coupled to at least one element in each row; and
a plurality of pulsers configured to provide high voltage pulses to the ultrasonic elements and the plurality of multiplexers;

a plurality of analog front-end receivers coupled to the multiplexers and configured to amplify and digitize received ultrasonic signals; and a control system coupled to the plurality of multiplexers, the plurality of high-voltage pulsers, and the plurality of analog front-end receivers, the controls system operable for imaging, using the array, a first zone by transmitting and receiving ultrasound signals using a multi-angle plane wave imaging scheme, the first zone having a depth dimension that extends from a surface of an object being imaged to a first depth into the object;

imaging, using the array, a second zone by transmitting and receiving ultrasound signals using a tissue harmonic imaging scheme, the second depth zone extending from the first depth to a second depth into the object, the second depth being farther from the surface of the object than the first depth, the first zone being between the second zone and the ultrasonic array, wherein imaging at least one of the first zone or the second zone includes forming a thick slice image of at least one of the first zone or the second zone;

imaging, using the ultrasonic array, a third zone by transmitting and receiving ultrasound signals in the third zone using fundamental and subharmonic deep imaging, the third zone extending from the second depth to a third depth farther from the surface of the object than the second depth, the second zone being between the first zone and the third zone;

forming an image based on the received signals from the first zone, the second zone, and the third zone;

extending at least one first patch from the second zone such that the at least one first patch overlaps with at least one first horizontally adjacent patch to form a first overlapping area;

extending at least one second patch from the third zone such that the at least one second patch overlaps with at least one second horizontally adjacent patch to form a second overlapping area;

blending the at least one first patch with the at least one first horizontally adjacent patch in the first overlapping area;

blending the at least one second patch with the at least one second horizontally adjacent patch in the second overlapping area;

extending at least one third patch from the second zone such that the at least one third patch overlaps with at least one vertically adjacent patch in the third zone to form a third overlapping area; and blending the at least one third patch with the at least one vertically adjacent patch in the third overlapping area.

* * * * *